(12) United States Patent
King et al.

(10) Patent No.: US 12,004,994 B1
(45) Date of Patent: Jun. 11, 2024

(54) DEVICE FOR HYPOTHERMIA THERAPY ON A COCHLEA

(71) Applicant: Restorear Devices, LLC, Kirkland, WA (US)

(72) Inventors: Curtis S. King, Kirkland, WA (US); Suhrud Rajguru, Coral Gables, FL (US)

(73) Assignee: Restorear Devices, LLC, Kirkland, WA (US)

( * ) Notice: Subject to any disclaimer, the term of this patent is extended or adjusted under 35 U.S.C. 154(b) by 617 days.

(21) Appl. No.: 17/139,962

(22) Filed: Dec. 31, 2020

(51) Int. Cl.
*A61F 7/12* (2006.01)
*A61F 7/00* (2006.01)

(52) U.S. Cl.
CPC .............. *A61F 7/123* (2013.01); *A61F 7/007* (2013.01); *A61F 7/0085* (2013.01); *A61F 2007/0005* (2013.01); *A61F 2007/0086* (2013.01); *A61F 2007/0092* (2013.01); *A61F 2007/0094* (2013.01)

(58) Field of Classification Search
CPC .. A61F 2007/0005; A61F 7/123; A61F 7/007; A61F 2007/0086; A61F 2007/0092; A61F 2007/0094
See application file for complete search history.

(56) References Cited

U.S. PATENT DOCUMENTS

| | | | | |
|---|---|---|---|---|
| 5,437,614 A | * | 8/1995 | Grim | A61F 5/022 602/8 |
| 7,335,222 B1 | | 2/2008 | Tyler | |
| 2005/0192652 A1 | * | 9/2005 | Cioanta | A61F 7/12 607/113 |
| 2015/0320591 A1 | * | 11/2015 | Smith | A61B 8/06 600/407 |

* cited by examiner

*Primary Examiner* — Tigist S Demie
(74) *Attorney, Agent, or Firm* — Brian C. Trask

(57) ABSTRACT

A device to change the temperature of a localized volume of material. One device includes at least one heat transfer mechanism having a conformable external surface for direct contact with a surface of the material. A working fluid is directed by input and output conduits to contact an internal surface of the heat transfer mechanism. A wall of the heat transfer mechanism exchanges heat between the working fluid and the material. Temperature of the working fluid may be regulated by a thermal control system disposed at a remote location. An optional temperature sensing element may monitor a local temperature of the heat transfer mechanism or otherwise infer a temperature of a portion of the material. Portions of certain devices may be deformed to a desired device shape.

18 Claims, 24 Drawing Sheets

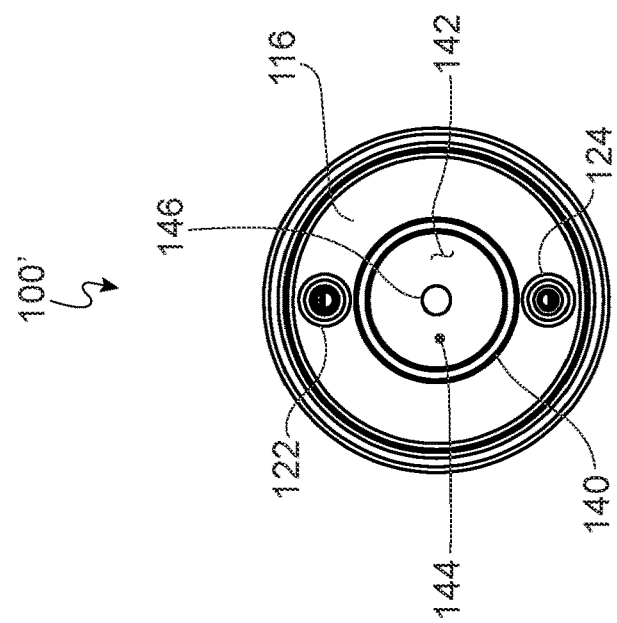
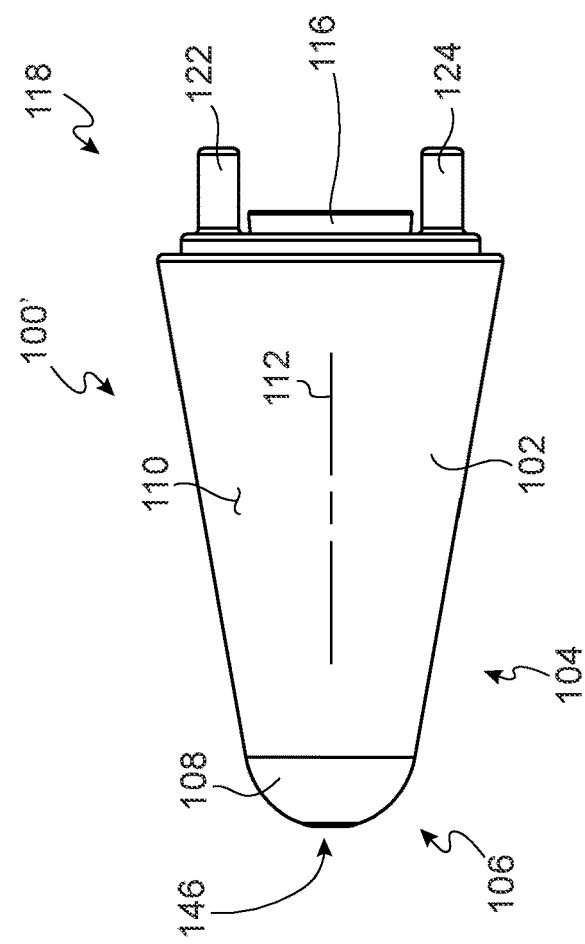
FIG. 6
FIG. 5

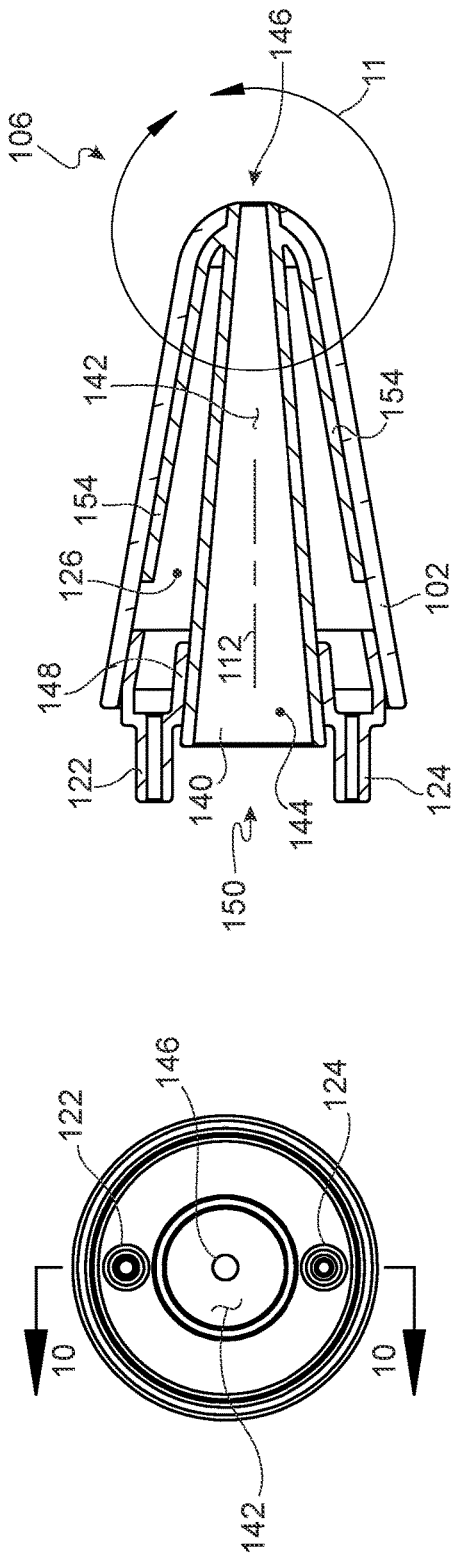
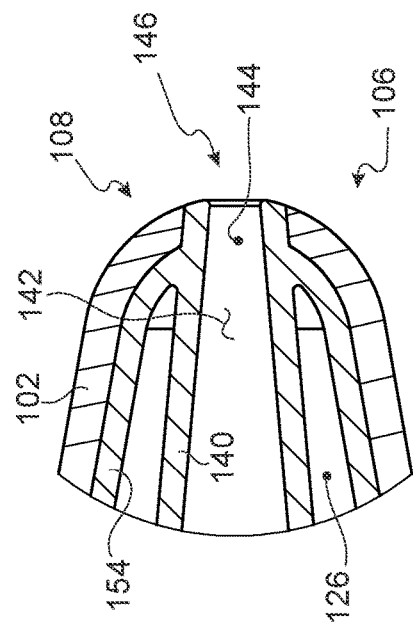
FIG. 9
FIG. 10
FIG. 11

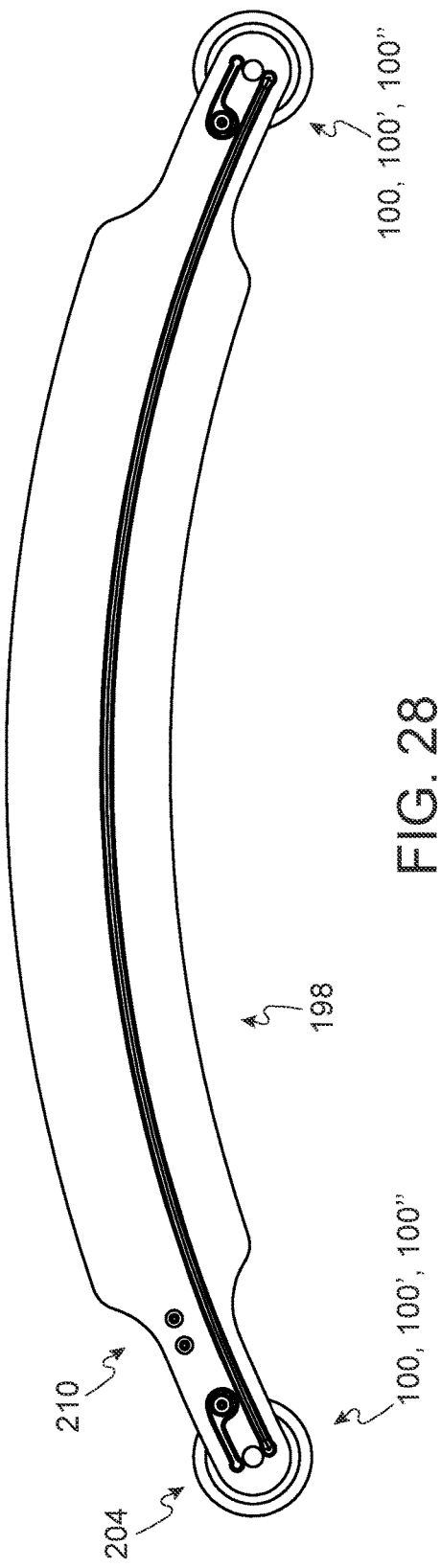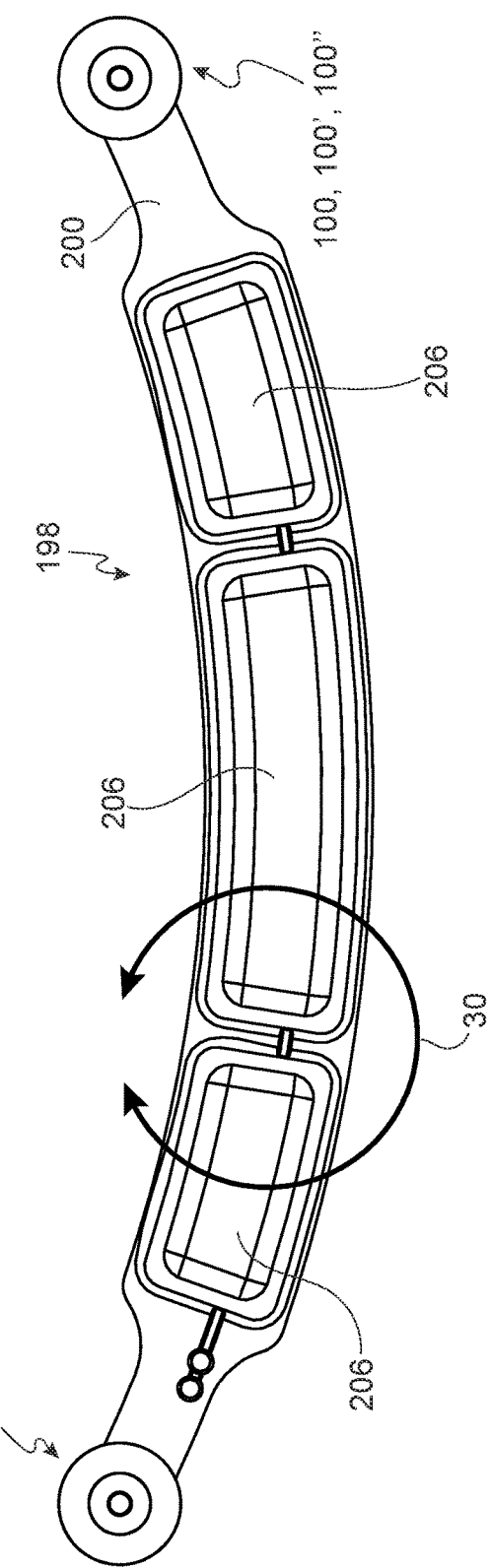

DEVICE FOR HYPOTHERMIA THERAPY ON A COCHLEA

BACKGROUND

Field of the Invention: This invention relates to devices configured to change the temperature of a localized area or volume of material. It is particularly directed to direct contact devices for cooling a subsurface portion of a medical patient's body to a controllable value having a magnitude of less than a conventional local body temperature.

State of the Art: Mild Therapeutic Hypothermia (MTH) has been shown to have benefits to human tissue and various physiological systems. Recently, it has been shown that MTH has otoprotective potential for the organs and structures of the human inner and outer ear. For example, the application of MTH during and after cochlear implant surgical procedures has been shown to improve procedural outcomes by improved preservation of residual (ie, natural) hearing.

Successful use of MTH during cochlear implant procedures depends on the ability to deliver the thermal therapy to a site in the skull with a thermal conduction pathway to the cochlea and the area around the cochlea. In the surgical procedure, this is achieved using a small cooling device positioned in a "pocket" feature in the skull created by the surgeon. This pocket feature allows the medical practitioner to place the thermal device in a specific site with a direct heat transfer pathway (via thermal conduction) through the temporal bone of the skull to the cochlea, where application of MTH decreases the regional temperature in the area of the cochlea from 37 degrees to 30-34 degrees C.

Use of MTH as non-surgical therapy for chronic hearing and balance conditions is contemplated herein. In these cases, it is unlikely there will be direct invasive access to the temporal bone (or other bones in the skull) or internal ear structures, and MTH will be applied percutaneously (external, through the skin) to areas of the skull or ear where a heat transfer pathway through bone to structures of the inner and middle ear exists. One potential site that provides direct access to the structures of interest is the ear canal. Tissue and bone structures in the canal and surrounding areas of the skull, combined with a lower regional tissue density, provide a reasonably direct heat transfer pathway (again, for thermal conduction) from the external skull, to the anatomical structures of the middle and inner ear. To provide consistent therapy, it is essential that the heat transfer pathway between the device and the tissue be consistent which is challenging from a device perspective. Because of variations in size and shape, and the presence in this region of external anatomical differences, it is convenient that any device designed to fit in the ear canal be shape/size adaptable, so that the fit, and in this case, the heat transfer pathway is consistent, for all users. Therefore, there exists in the art the need for a medical device designed to adjustably fit in the human ear canal so that MTH can be delivered through the ear canal to the structures of the middle and inner ear.

BRIEF SUMMARY OF THE INVENTION

This invention provides a heat transfer mechanism with an external surface to contact a portion of a material to effect temperature change on a local portion of that material. Here, the term "local" is used to distinguish over systemic temperature modification. The heat transfer mechanism desirably includes a transversely flexible portion to conform to an undulating or irregular surface. Heat transfer into, or out of, the material is primarily by way of conduction between the material and a working fluid circulating through the mechanism. The volume of temperature-regulated material produced by operation of devices according to certain principles of this invention may be relatively small, e.g., on the order of a 1 to 2 cm diameter sphere.

The invention may be embodied to include a flexible heat exchanger approximately sized to the dimensions of the human ear canal, shape deformable such that a mechanically compressible fit between the device and human ear canal may be achieved when installed. Alternatively, or in addition, a suitable fit may be achieved by inflating a portion of a heat exchanger. The preferred flexible body has at least 1 internal fluidically-sealed chamber, into and through which circulating working fluid is driven by an external flow control system. A workable flow control system typically includes, 1) a pump, 2) a flow sensor, 3) a microcontroller, 4) a temperature sensor, and 5) a refrigeration or some alternative thermal control source that interfaces or reacts with circulating heat transfer fluid. One flexible heat exchanger is typically placed in each ear, and the heat exchangers are connected to the flow control system. In a first configuration, working fluid circulates between the flow control system and each ear canal's device separately, in a parallel loop fashion. In a second embodiment, the two heat exchanger devices may be connected fluidically in series. In the fluidically in series configuration, working fluid circulates from the flow control system in series to a first device (located in the first ear), then to the second device (located in the second ear), and back to the flow control system.

The thermal or working fluid may be either a gas or a liquid. In the liquid case, the fluid temperature is generally controlled and pumped in closed loop fashion, from the flow control system into each ear canal device. Heat transfer between the heat exchangers and the tissue of the ear canal results cooling of the middle and inner ear structures. For the case of a gaseous cooling fluid, circulating fluid undergoes compression and expansion, resulting in rapid cooling. The gas circulates between the flow control system and each ear canal device resulting in thermal transfer from the device to the middle, and eventually inner ear structures.

An embodiment generally includes at least one heat exchanger configured to fit in generally comfortable registration inside an ear canal of a human. A workable first heat exchanger includes an insertable part configured and arranged to fit into the ear canal for operable disposition exterior to the ear drum associated with that ear canal. An exemplary heat exchanger includes a heat transfer surface disposed radially with respect to a length axis of the first heat exchanger. A portion of the heat transfer surface may be placed into contact with a heat transfer area of the ear canal. Desirably, the heat transfer surface provides transverse flexibility to deflect and conform for contact to a generally cylindrical heat transfer area of the inner surface of the ear canal. A heat transfer surface may sometimes be compressed into a desired fit, or may be expanded into the desired fit.

A fluid-holding cavity typically extends along a portion of the length axis of a heat exchanger, the cavity being configured and arranged to receive a working fluid for disposition of the fluid in operable proximity to the heat transfer surface. A cavity may be formed by a membrane element, like a balloon wall, or other transversely deflectable wall-type of element.

A currently preferred embodiment includes a fluid input port in fluid communication with a fluid-holding cavity to introduce working fluid to the cavity. A proximal portion of the input port can be configured to couple with a first end of a fluid-transporting conduit. The embodiment may also include a fluid output port in fluid communication with the fluid-holding cavity to exhaust the working fluid. A proximal portion of the output port can be configured to couple with a second end of a fluid-transporting conduit, or with an alternative conduit.

A workable heat exchanger may include a non-traumatic tip disposed at its distal insertable end to resist causing damage to sensitive tissue.

Certain heat exchangers further include a sonic conduit extending to an opening associated with the distal end of the insertable part. Desirably, the sonic conduit is configured and arranged to provide an unobstructed air path from exterior the ear, through the heat exchanger, and toward the ear drum. A currently preferred sonic conduit resists undue attenuation of sound transported toward the eardrum of a medical patient with an installed heat exchanger.

One operable heat exchanger includes a generally annular and elongate core with an inner surface disposed spaced apart from a length axis by a radial function. A currently preferred core provides a sonic conduit to avoid undue attenuation of sound received by an eardrum. One exemplary core carries a plurality of transversely flexible support arms, the support arms to form a framework to hold an inner surface of the heat transfer surface at an initial position, and to accommodate subsequent transverse deflection of the heat transfer surface during installation of the insertable part into the ear canal.

A workable heat exchanger may include a proximal end cap. An end cap can be associated with a proximal end of a core element. One workable proximal end cap provides grippable structure to facilitate tool-free removal of the insertable part from an ear canal. In certain embodiments, the proximal end cap can provide a cantilever base from which the core extends. A proximal end cap may include an opening at the proximal end of the proximal end cap to provide fluid communication to a sonic conduit through the core and extending to an opening associated with the distal end of the insertable part.

Certain embodiments includes a first fluid path to provide fluid communication with one of an input fluid port and an output port, the first fluid path extending through a portion of the core. Embodiments may also include a second fluid path to provide fluid communication with the other one of the input fluid port and the output port. Sometimes, the first fluid path extends to an opening associated with a distal portion of the core. Other times, the first fluid path extends to an opening associated with a proximal portion of the core.

A currently preferred core includes at least one fluid-directing conduit element associated with at least one of the input port and the output port. Such fluid-directing conduit can be arranged to promote flow of the working fluid in a length axis direction such that working fluid flows through the heat transfer area predominately from the proximal end toward the distal end of the insertable part, or, from the distal end toward the proximal end of the heat transfer area. In other embodiments, a fluid input port and a fluid output port may simply be disposed on opposite sides of a core, the core comprising a portion extending from the proximal end of the insertable part toward the distal end of the insertable part, the core to promote fluid travel through the cavity in a length direction of the insertable part. A workable embodiment may include input and output ports that are spaced apart across an end of an uninterrupted cavity.

A heat transfer surface may be affixed at its proximal end to a proximal end cap, or to a core element. A workable heat transfer surface may include a portion of a generally annular balloon affixed at a proximal balloon end to the proximal end of the core, the exterior annular wall being transversely flexible to accommodate to a variable wall conformation of the ear canal, a portion of the inner annular wall being affixed to the core. The balloon can sometimes be a generally annular balloon, or may be a single-wall element. In the case where the balloon is generally annular, an inner wall of the balloon may include an input port opening and an output port opening, the input port opening being arranged for fluid-tight communication with the input port, the output port opening being arranged for fluid-tight communication with the output port.

A workable heat transfer surface may include a portion of a balloon wall, a proximal balloon end being affixed to either the proximal end of the core or to structure associated with a proximal end cap. An embodiment may include a generally annular and elongate core with an exterior surface disposed spaced apart as a radial function from the length axis, an inner surface being spaced apart from the length axis to provide a sonic conduit configured and arranged to provide an unobstructed air path from exterior the ear toward the ear drum.

Certain embodiments may include a second heat exchanger with an insertable portion configured and arranged for installation in the other ear canal of the human. Embodiments may include a temperature monitoring transducer associated with at least one of the first heat exchanger and the second heat exchanger to infer temperature of a portion of an ear canal. Embodiments may include a pressure monitoring transducer associated with at least one of the first heat exchanger and the second heat exchanger to monitor inflation status of a heat exchanger and/or a padding bladder.

Certain embodiments include an elongate support band with a first band end and a second band end, the first heat exchanger being held in association with the first band end, the second heat exchanger being held in association with the second band end, the support band being deformable to provide an arcuate shape in which to receive a human head to dispose the first heat exchanger in installed registration in one ear canal and the second heat exchanger in installed registration in the other ear canal. Typically, conduits are provided to convey working fluid from a remote temperature controller toward and away from each heat exchanger. A workable band may include a pneumatic padding bladder carried at an intermediate position by the support band, the bladder being inflatable to provide a variable-size filler between a portion of the support band and a human head received in the arcuate shape.

BRIEF DESCRIPTION OF THE DRAWINGS

In the drawings, which illustrate what are currently considered to be the best modes for carrying out the invention:

FIG. 5 is a side view in elevation of an embodiment;

FIG. 6 is a proximal end view in elevation of the embodiment in FIG. 5;

FIG. 9 is a rear view in elevation of the embodiment in FIG. 5;

FIG. 10 is the cross-section view indicated by arrows 10-10 in FIG. 9;

FIG. 11 is a close-up view of the portion indicated by circle 11 in FIG. 10;

FIG. 28 is a rear view of the assembly in FIG. 27;

FIG. 29 is a front view of the assembly in FIG. 27;

DETAILED DESCRIPTION OF THE ILLUSTRATED EMBODIMENTS

Reference will now be made to the drawings in which the various elements of the illustrated embodiments will be given numerical designations and in which the invention will be discussed so as to enable one skilled in the art to make and use the invention. It is to be understood that the following description is only exemplary of certain principles of the present invention, and should not be viewed as narrowing the claims which follow.

Figure 1:
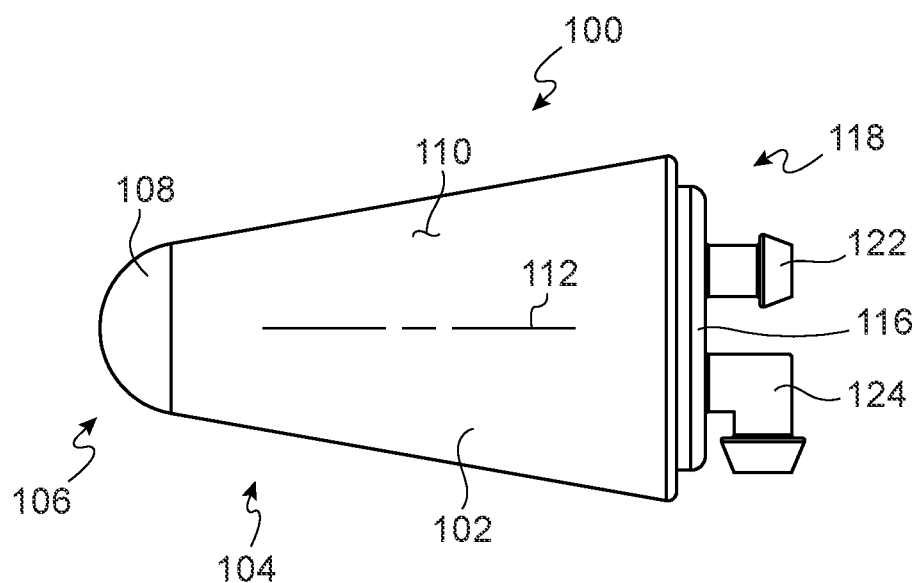
FIG. 1 is a side view in elevation of an embodiment structured according to certain principles of the instant invention.
Figure 2:
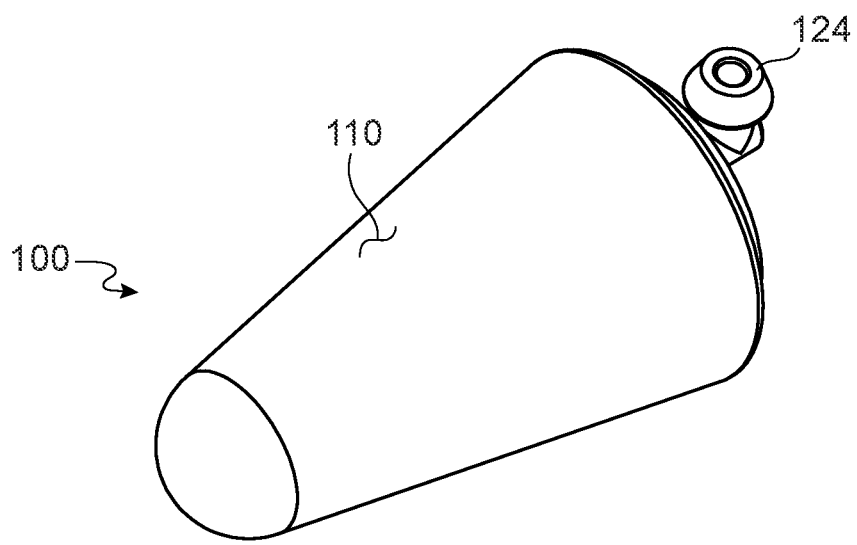
FIG. 2 is a front perspective view from below of the embodiment in FIG. 1.
Figure 4:
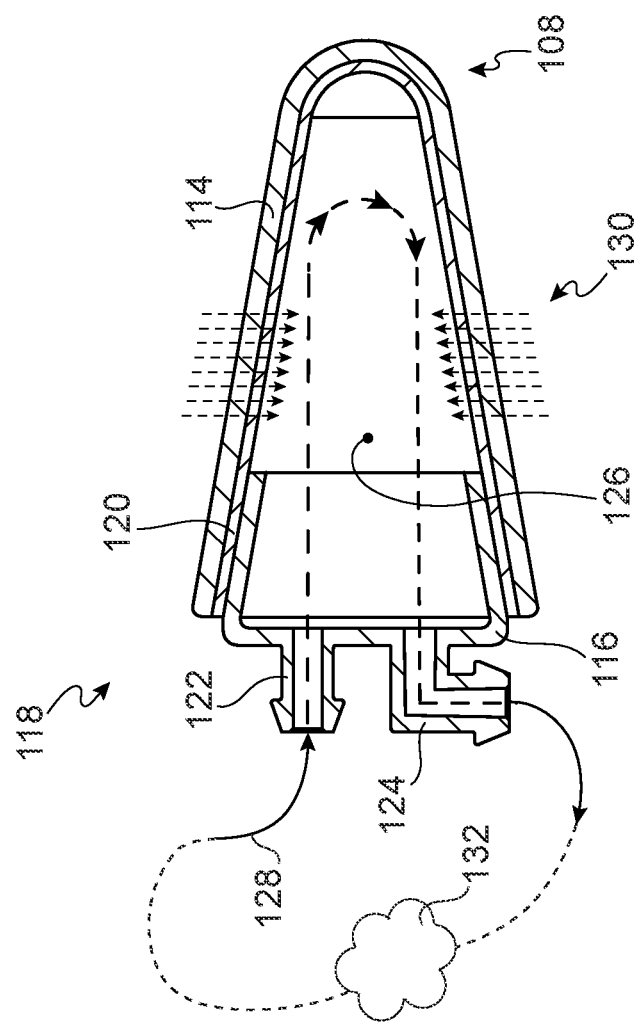
FIG. 4 is a cross-section view of the section indicated at 4-4 in FIG. 3, and looking in the direction of the arrows.
Figure 3:
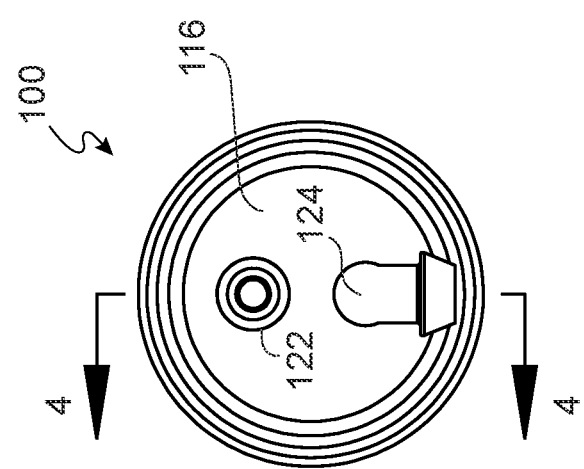
FIG. 3 is a rear view in elevation of the embodiment in FIG. 1.
Figure 7:
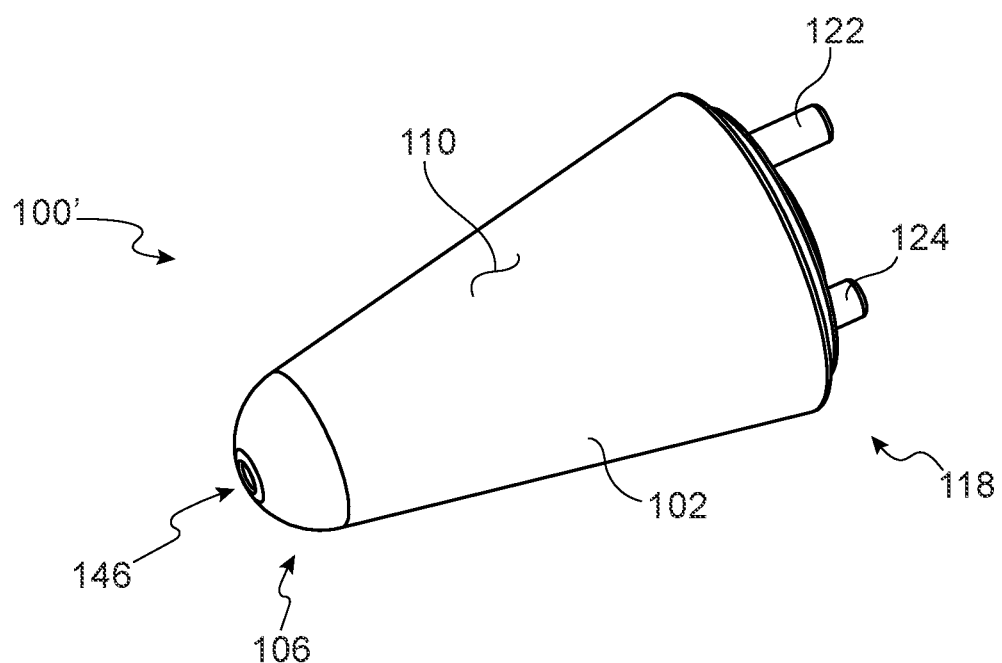
FIG. 7 is front perspective view of the embodiment in FIG. 5.
Figure 8:
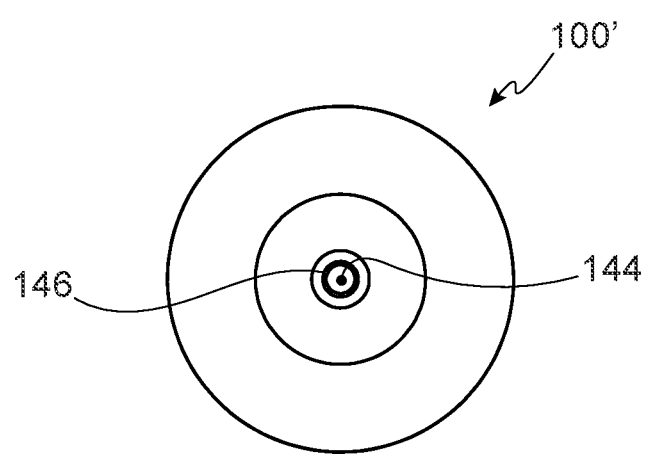
FIG. 8 is a front view in elevation of the embodiment in FIG. 5.

An embodiment according to certain principles of the invention is illustrated generally at 100 in FIG. 1. Embodiment 100 is operable as a heat exchanger to change and desirably regulate the temperature of a local volume of material. For purpose of this disclosure, a device such as heat exchanger 100 may be made reference to as a cooling device. However, it is to be understood that a heat exchanger, such as illustrated at 100, may find equal utility as a heating device. Other workable devices may be regarded as thermal regulating devices, and may be capable of heating or cooling, or alternating between the two. Certain currently preferred devices described herein are applied to cooling local volumes of tissue, including living animal tissue. Consequently, this disclosure may make reference to the thermally regulated material as tissue. It is to be understood that heat exchanger devices according to certain principles of the invention may be applied as well to alternative substrates.

With reference to FIGS. 1-4, heat exchanger 100 includes an elongate body 102 with an insertable part, generally 104, configured and arranged to fit into an ear canal (or other orifice) of a human. Devices for use in an ear canal are configured for disposition exterior to the ear drum associated with that ear canal. The distal end, generally 106, of body 102 is desirably configured to provide a non-traumatic and soft tip to avoid damage to the canal during insertion and removal of the insertable part into an ear canal. Body 102 provides an exterior surface 110 that is deformable (e.g., transversely flexible, squishable or compressible, sometimes expandable or stretchable), to deflect and conform for contact to the inner surface of the ear canal. The illustrated surface 110 is disposed radially with respect to a length axis 112, and provides a portion that is operable as a heat transfer surface. Desirably, the insertable portion 104 is configured to effectively flex or bend along the length axis 112 to provide a comfortable accommodation to the nonlinear conformations of a variety of ear canals.

A workable body 102 may be embodied to include a bladder 114 sealed by an end cap 116 at a proximal end, generally 118. A leak-sealing element 120, such as adhesive, may be present to affix a bladder 114 to an end cap 116. As illustrated, leak-sealing element 120 may, in some form, extend distally to provide or to enhance fluid-holding capability of a bladder 114. A bladder 114 may be affixed to an end cap 116 in other ways to form a fluid-tight connection, including well known manufacturing processes such as friction welding, etc.

As illustrated, an input/output fluid port 122 is disposed in fluid-tight registration with respect to the end cap 116. A cooperating output/input fluid port 124 is also disposed in fluid-tight registration with respect to the end cap 116. The fluid ports cooperate to direct flow of a working fluid into, and out of, a cavity 126 defined inside body 102 (see FIG.

4). In the illustrated embodiment 100, working fluid 128 may flow in either direction through either fluid port. Discharge openings of the fluid ports into cavity 126 may be configured to promote mixing of working fluid inside cavity 126, or otherwise to control flow of working fluid with respect to a heat transfer zone. Heat, generally 130 may be transferred from a contacted tissue, through a wall of the bladder 114, and into the working fluid 128. Working fluid 128 is typically plumbed to and from the heat exchanger 100 through appropriate conduit elements (not illustrated) for temperature control of the working fluid by a remote thermal controller 132.

The tissue contact material of a body 102 may be silicone, foam, or some other thermally conductive, flexible polymer. The shape of a heat exchanger 100 has definition and is somewhat rigid axially, but desirably is easily deformed transversely as it is inserted into the ear canal. Working fluid enters and exits the device 100 through the input/output (I/O) ports 122, 124. The internal fluid-passing diameters of the I/O ports 122, 124 may be equal, or they may be different. That is, ports may be sized as desired to achieve directional fluid flow through the circuit, e.g., depending on the configuration and number of the respective heat exchangers in-circuit and the flow control system. In one case, a back-pressure may be used to inflate a balloon for contact of an exterior balloon surface with desired tissue for heat transfer.

An embodiment of a heat exchanger according to certain principles of the invention is illustrated generally at 100' in FIGS. 5-16. Heat exchanger 100' includes certain elements discussed above with respect to embodiment 100, and they are numbered accordingly.

Figure 12:
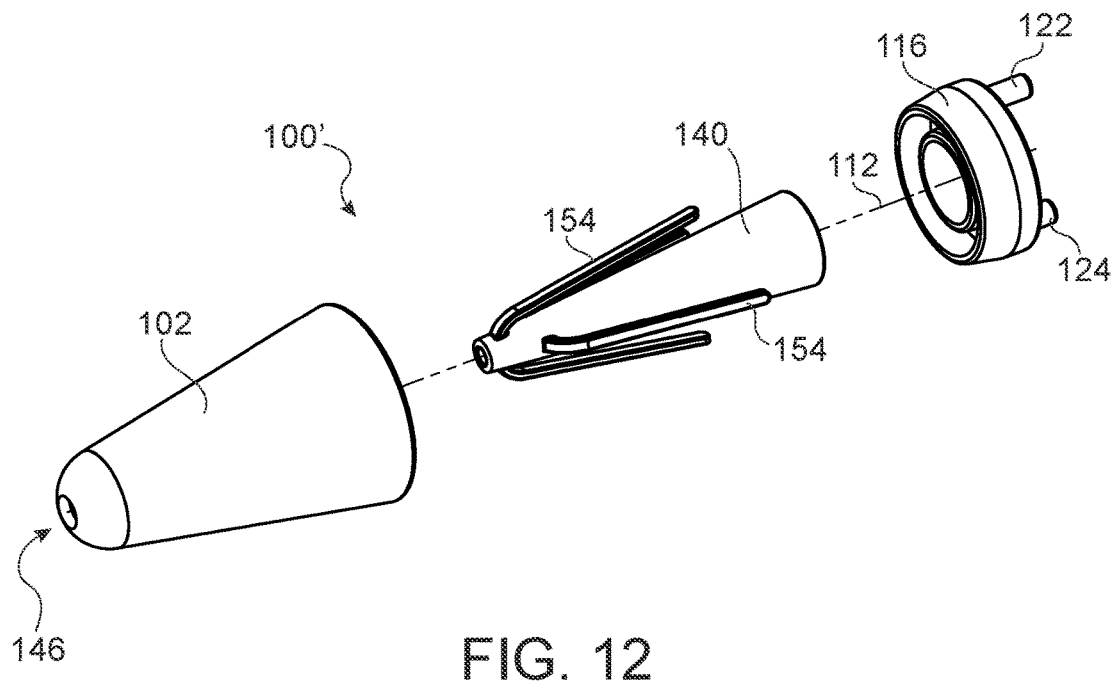
FIG. 12 is an exploded assembly view in perspective of the embodiment in FIG. 5.
Figure 13:
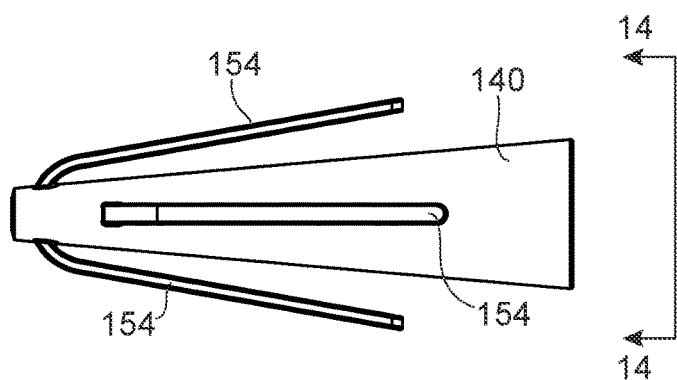
FIG. 13 is a side view in elevation of a core element of the embodiment in FIG. 5.
Figure 14:
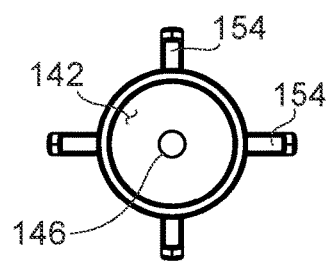
FIG. 14 is a proximal end view of the core element in FIG. 13.
Figure 16:
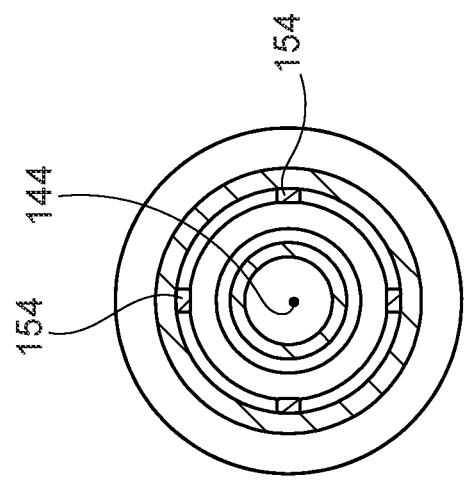
FIG. 16 is the cross-section view indicated at 16-16 in FIG. 15, and looking in the direction of the arrows.
Figure 15:
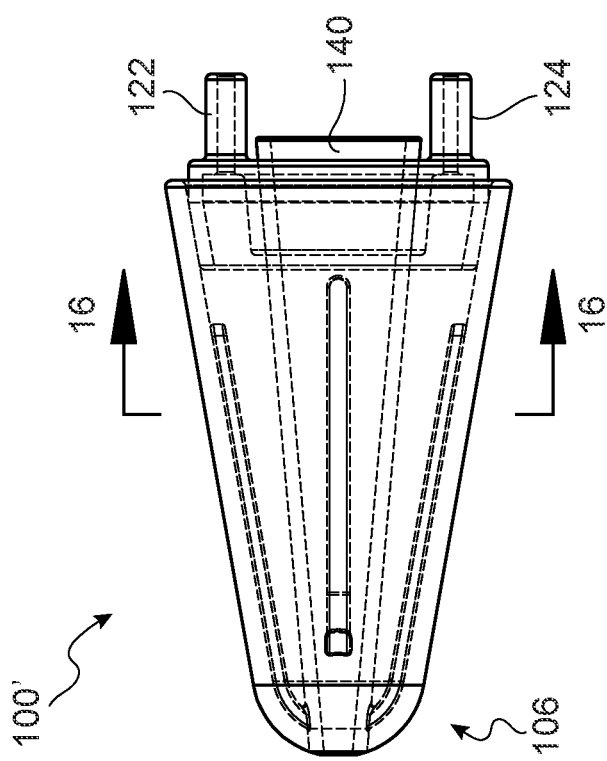
FIG. 15 is a side view in elevation of a translucent version of the embodiment in FIG. 5.

With particular reference to FIGS. 6, 10, and 12, heat exchanger 100' includes a generally annular and elongate core 140 with an inner surface 132 that is radially spaced apart from the length axis centerline 112 to provide at least a portion of a sonic conduit 144. Spacing between a local portion of the core 140 and centerline 112 can be a radial function depending on axial or circumferential position. Desirably, core 140 is configured to provide a beam along a length axis 112, the beam being bendable to conform to a nonlinear path through a portion of an ear canal. Workable materials of construction for a core 140 include various rubber compounds, silicone formulations, low durometer plastics, plastic- or rubber-like formulations, combinations thereof, and the like. It is even within contemplation that flexible metal portions may be included in a core 140 or other body-supporting element.

Sonic conduit 144 establishes an open air path extending, as illustrated, from a proximal position exterior the heat exchanger 100', along a length of the heat exchanger, and exiting through a distal opening 146 toward an eardrum. A sonic conduit 144 may sometimes be formed as a combination of various elements to provide the desired continuous and unobstructed open air path. A workable sonic conduit 144 functions to permit a patient undergoing a thermal treatment from an installed heat exchanger 100' to hear sounds without undue attenuation. Desirably, an installed device may reduce sound transmission levels by about 5-10 dB, or less. A sonic conduit 144 may be configured to receive insertion of at least one medical probe to permit performance of a procedure inside the ear canal, such as manipulation of tissue distal to the non-traumatic tip 108 of an installed heat exchanger 100'. For example, the sonic conduit 144 may be used to pass tools, optics, suction, etc, through the device 100' to access a surgical site in the ear canal.

As shown in e.g., FIG. 10, proximal end cap 106 provides a cantilever base element 148 from which the core 140 extends. An opening, generally 150 at the proximal end of the proximal end cap 106, provides fluid communication into sonic conduit 144 and extending through the core 140 to opening 146 associated with the distal end of the inserted portion of heat exchanger 100'.

A support arrangement for a membrane-like body 102 is shown with particular reference to FIGS. 12-16. The core 140 of heat exchanger 100' carries a plurality of optional transversely flexible cantilever struts or beams 154 to define an initial general shape for a somewhat drapeable or membranous body 102. The flexible body 102 and (when present) flexible arms 154 cooperate to provide an insertable part of a heat exchanger that is comfortable for a patient to receive in registration inside an ear canal.

As illustrated in FIG. 10, a fluid flow path between input/output port 122 and output/input port 124 must accommodate the core 140, thereby enhancing flow of working fluid in-and-out along axial (length) directions and passing along the inside surface of the body 102. Fluid input to cavity 126 in heat exchanger 100 may swirl in a flow path bending toward the output port. Effectively, the core 140 displaces fluid in the central area of the cavity 126, and presents a boundary to guide fluid flow in an axial direction. Presence of a core 140 encourages fluid to flow axially over an extended portion of body 102 toward the distal end 106, increasing total heat transfer through a wall of body 102. Therefore, the heat transfer capacity or efficiency of heat exchanger 100' may be more effective or enhanced, compared to heat exchanger 100.

Figure 17:
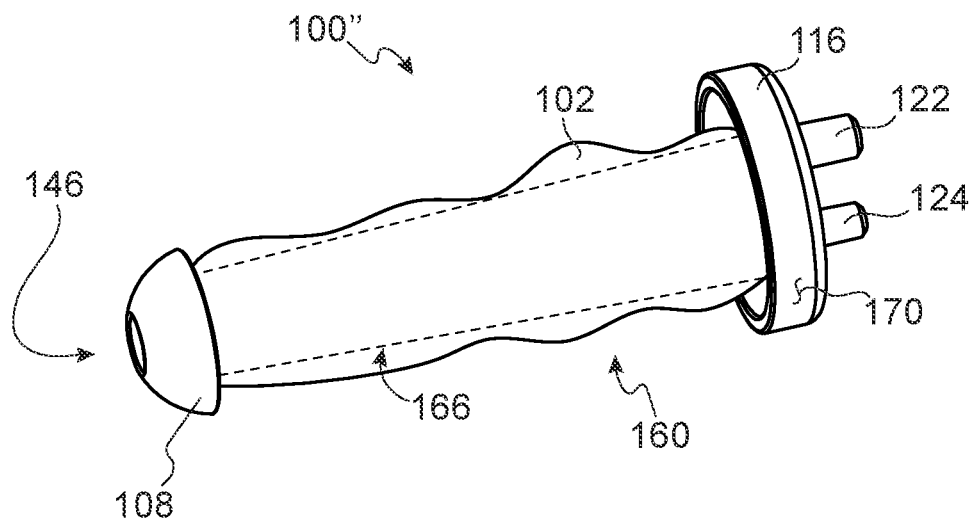
FIG. 17 is a view in perspective of an embodiment in a deflated configuration.
Figure 18:
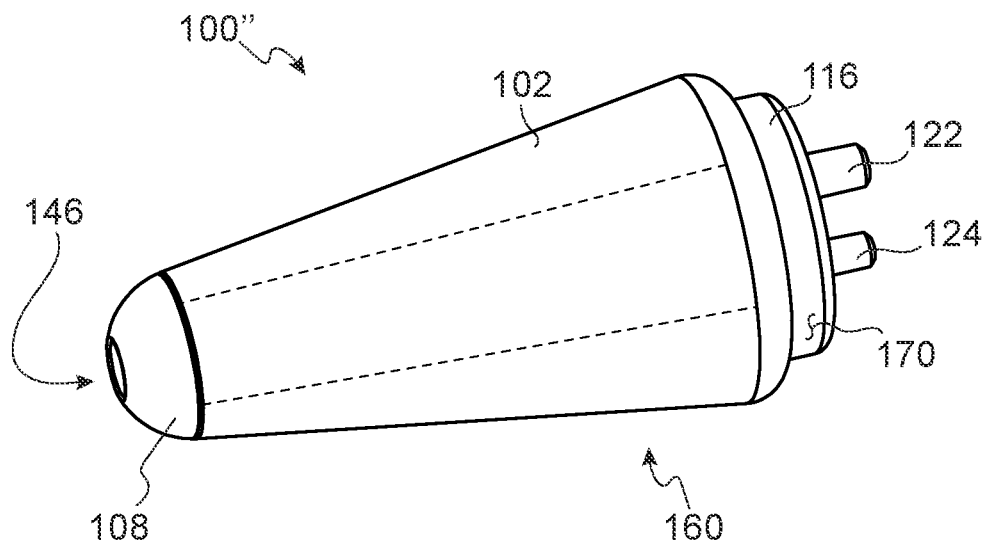
FIG. 18 is a view in perspective of the embodiment in FIG. 17, in an inflated configuration.

FIGS. 17-26 illustrate details of construction for heat exchanger 100", including a body 102 formed as a generally annular balloon, generally 160. For purpose of this disclosure, a generally annular balloon 160 has an inner wall with a surface 162 and an outer wall 164. Outer wall 164 carries the exterior surface 110. An inflatable cavity 126 is formed between the two balloon walls. In FIG. 17, the illustrated balloon 160 is affixed to a core 140, and arrow 166 is pointing out the boundary (dashed line) where the inner wall of balloon 160 is in contact with a supporting surface of the core 140.

In certain embodiments, proximal cap 116 provides an interface surface 170 to facilitate gripping the proximal end of a heat exchanger to remove it from an installed position in an ear canal. A workable cap 116 may be formed from plastic, e.g., injection molded. Even so, it remains desirable for the end cap 116 and other structure of a heat exchanger to be sufficiently flexible to enhance user comfort with respect to an installed heat exchanger 100'.

Figure 19:
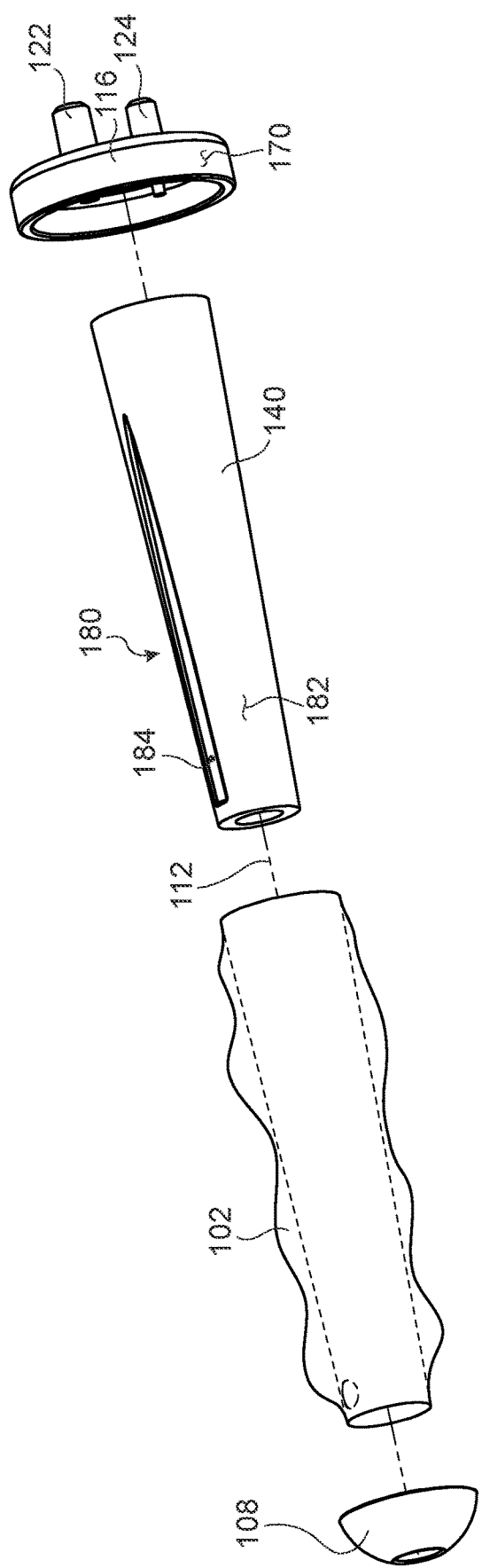
FIG. 19 is an exploded assembly view in perspective of the embodiment in FIG. 18.
Figure 20:
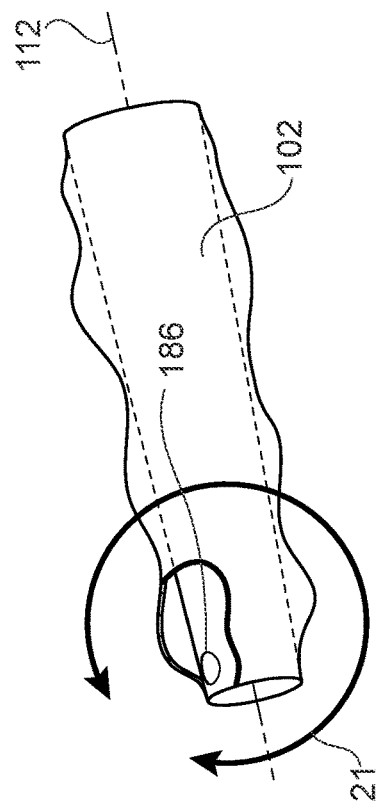
FIG. 20 is a view in perspective of a balloon element of the embodiment in FIG. 18.
Figure 21:
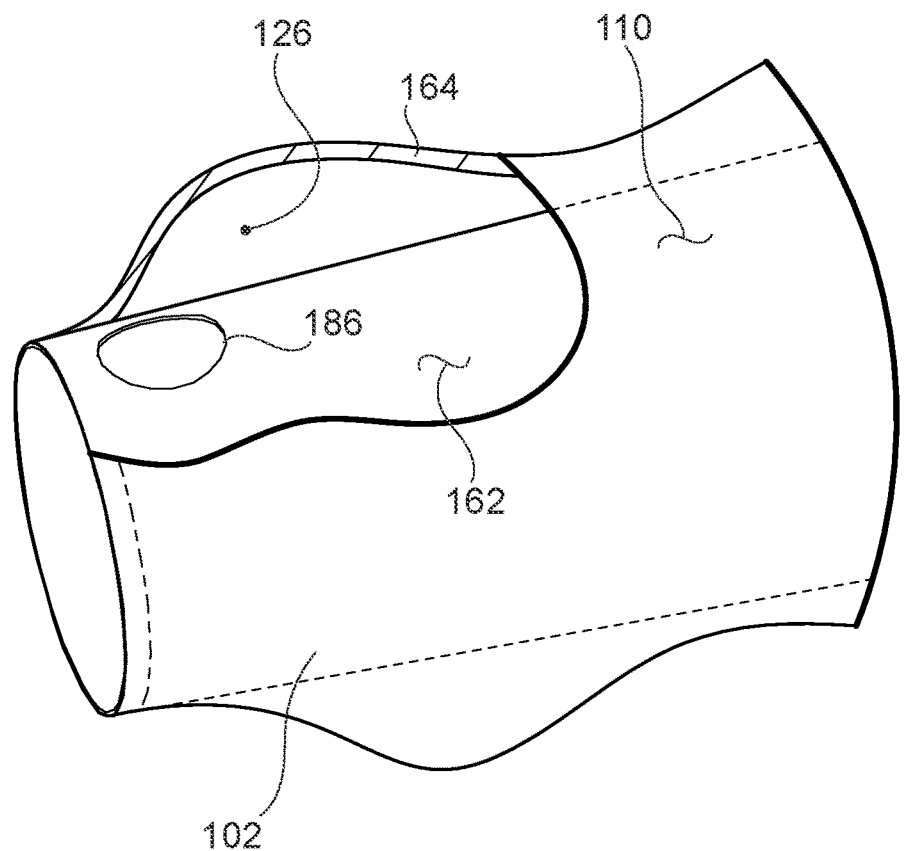
FIG. 21 is a close-up view of the portion indicated by circle 21 in FIG. 20.
Figure 22:
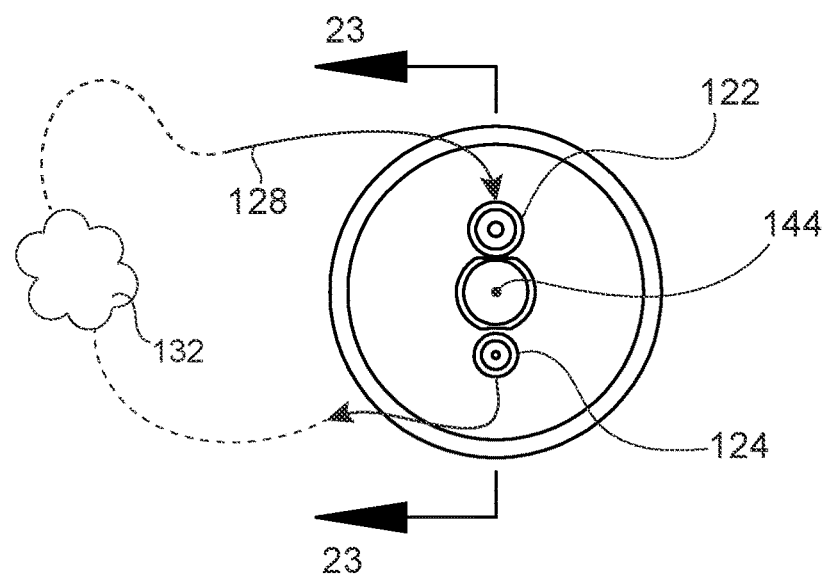
FIG. 22 is a proximal end view of core and end cap elements of the embodiment in FIG. 18.
Figure 23:
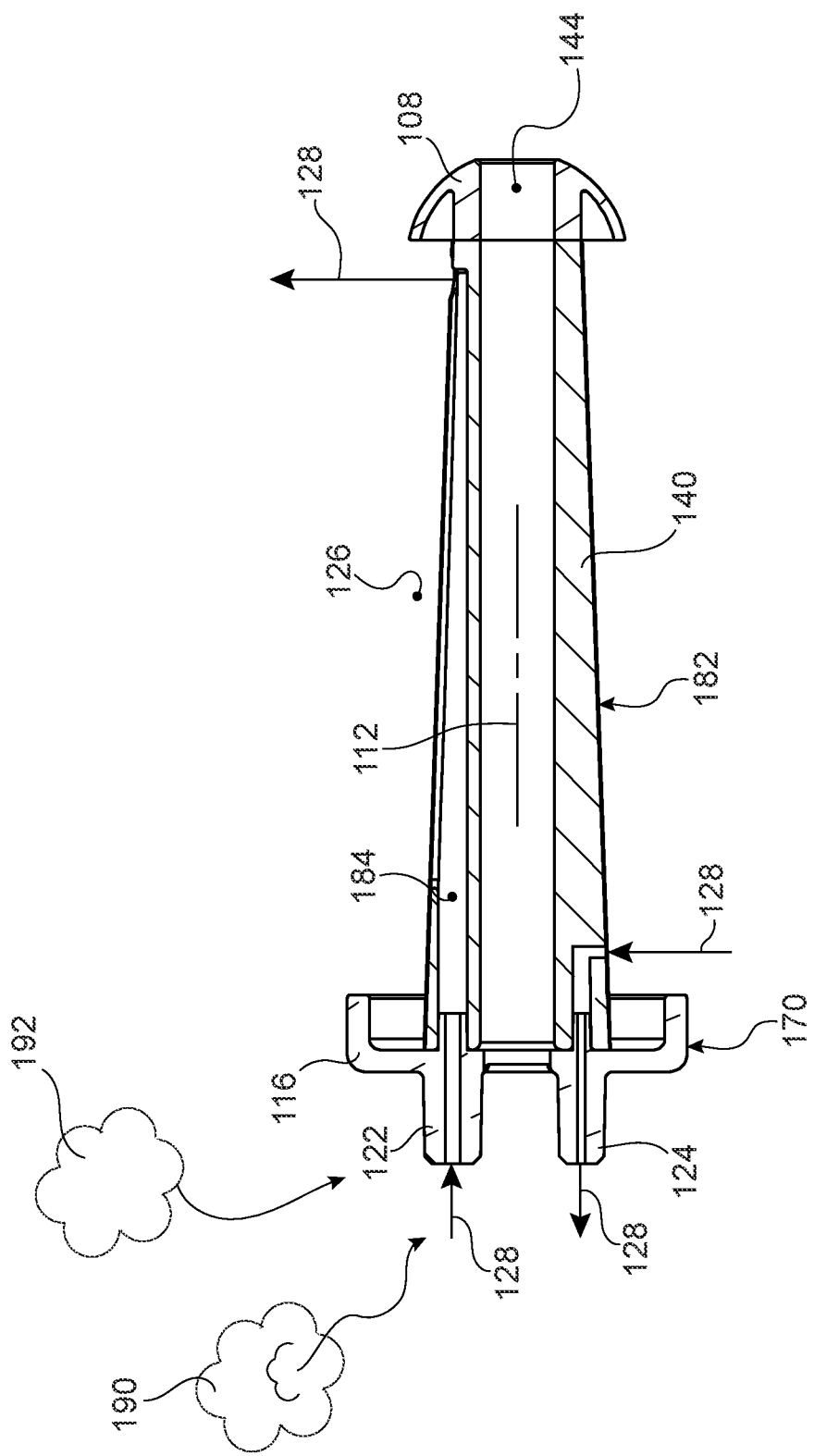
FIG. 23 is the cross-section view 23-23 indicated in FIG. 22, and looking in the direction of the arrows.

Heat exchanger embodiment 100" illustrates elements arranged to deliver a workable third exemplary flow pattern for working fluid 128. As seen in FIGS. 19, 22 and 23, core 140 carries a slot, generally 180, that is partially internal to the core and partially exposed. A slot 180 may be created in a plastic injection mold, for example, by a cylindrical slide or ejector core that bisects the external face 182 of the core 140. Conduit 180 defines a portion of a fluid flow conduit 184 that extends from a distal end of core 140 proximally to a proximal opening of input/output port 122.

Figure 24:
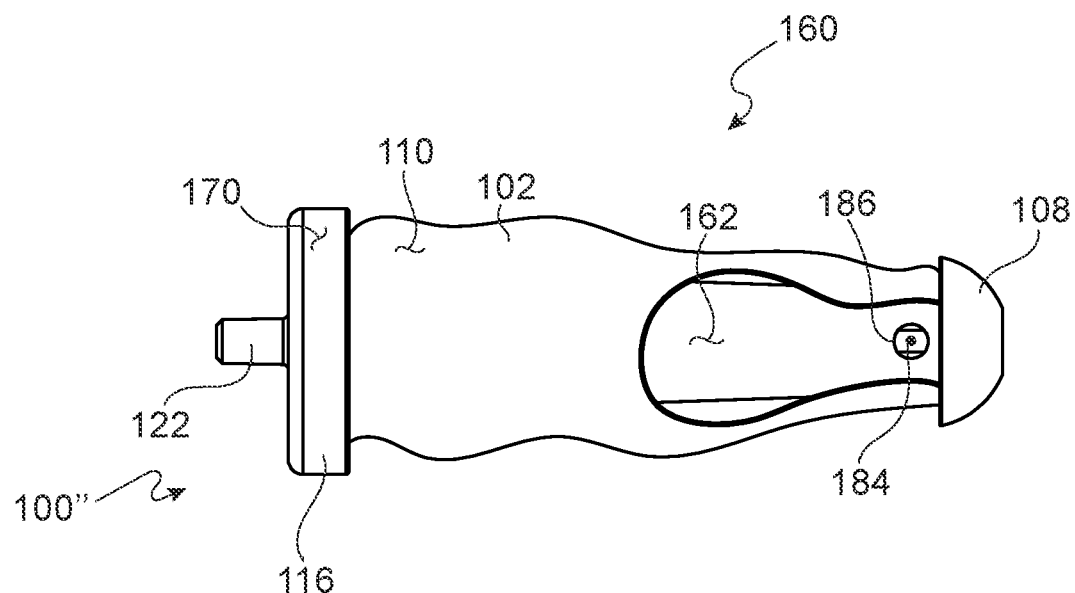
FIG. 24 is a side view of the embodiment in FIG. 18, with a section removed to present a view at internal distal structure.
Figure 25:
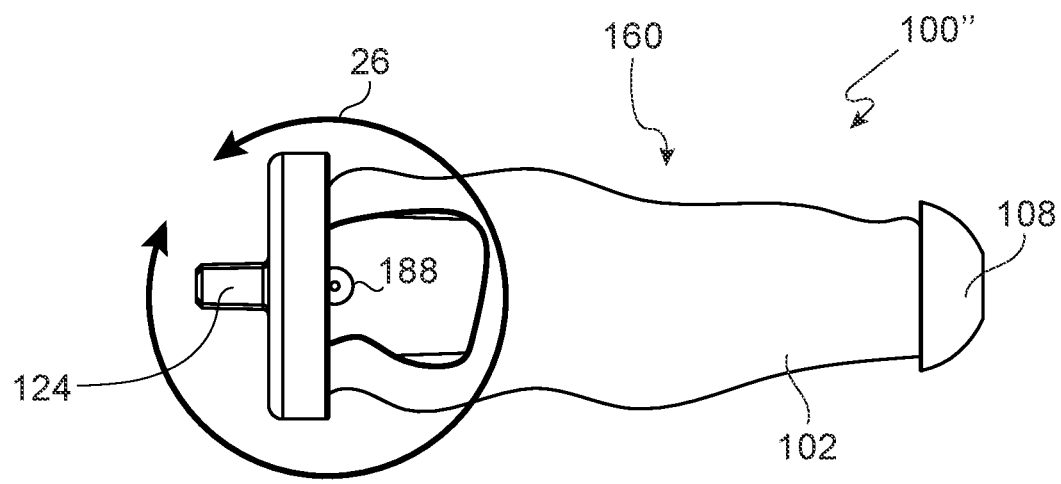
FIG. 25 is a side view of the embodiment in FIG. 18, with a section removed to present a view at internal proximal structure.
Figure 26:
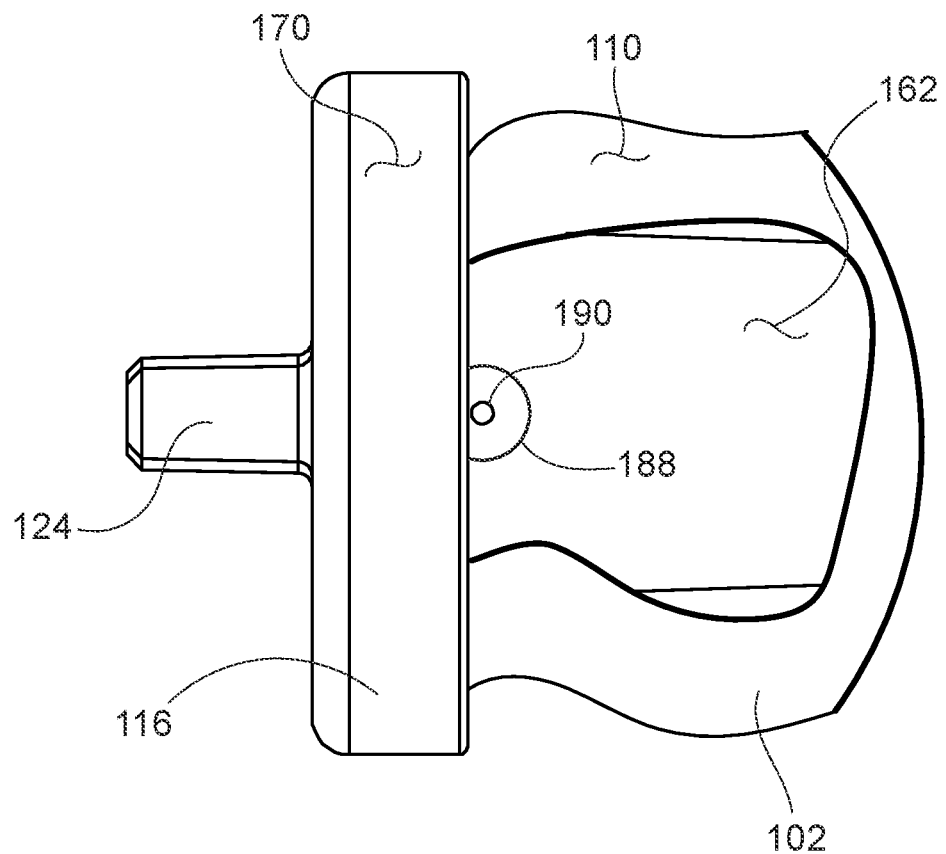
FIG. 26 is a close-up view of the portion indicated by circle 26 in FIG. 25.
Figure 27:
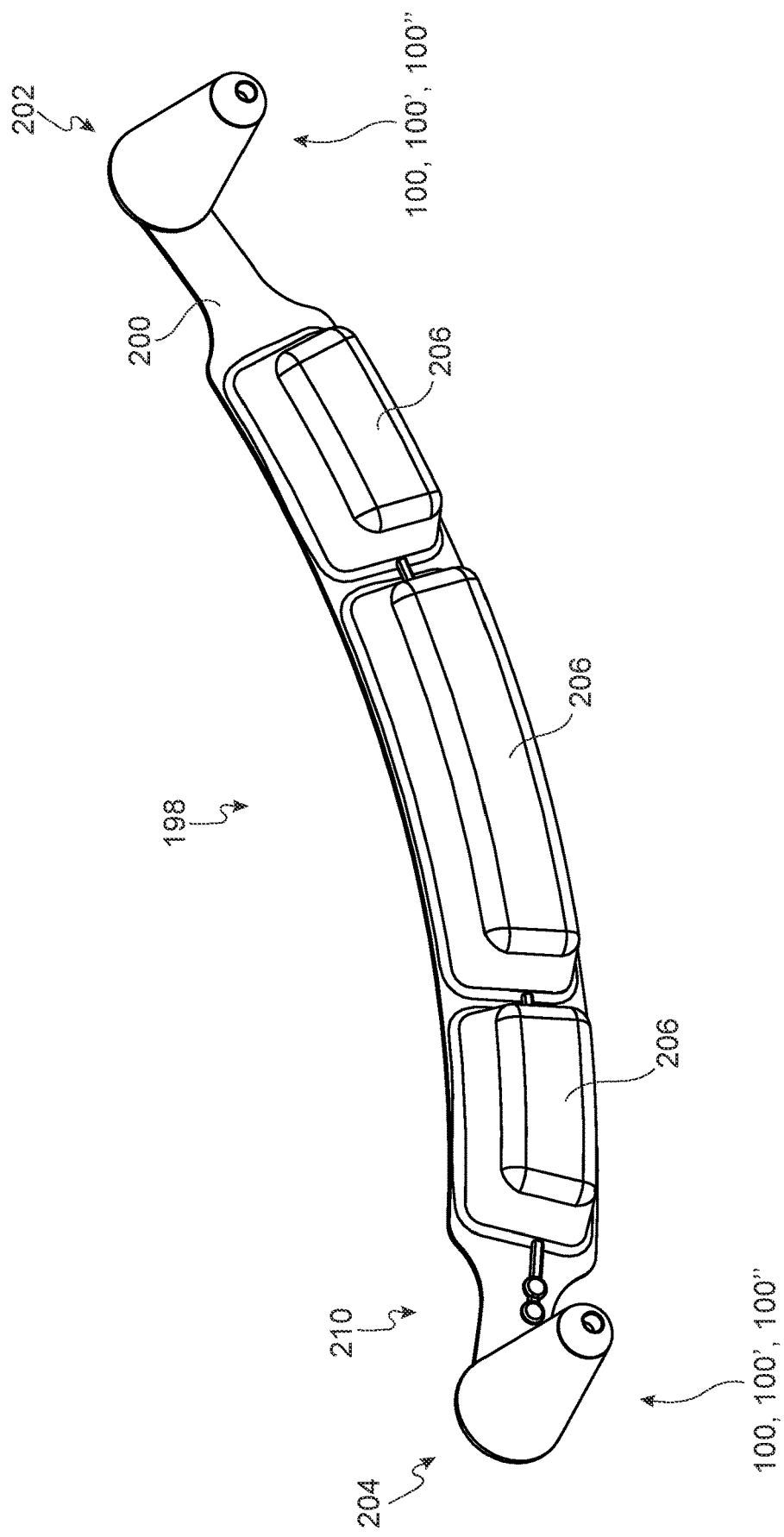
FIG. 27 is a view in perspective of an assembly including previously illustrated heat exchanger(s)
Figure 30:
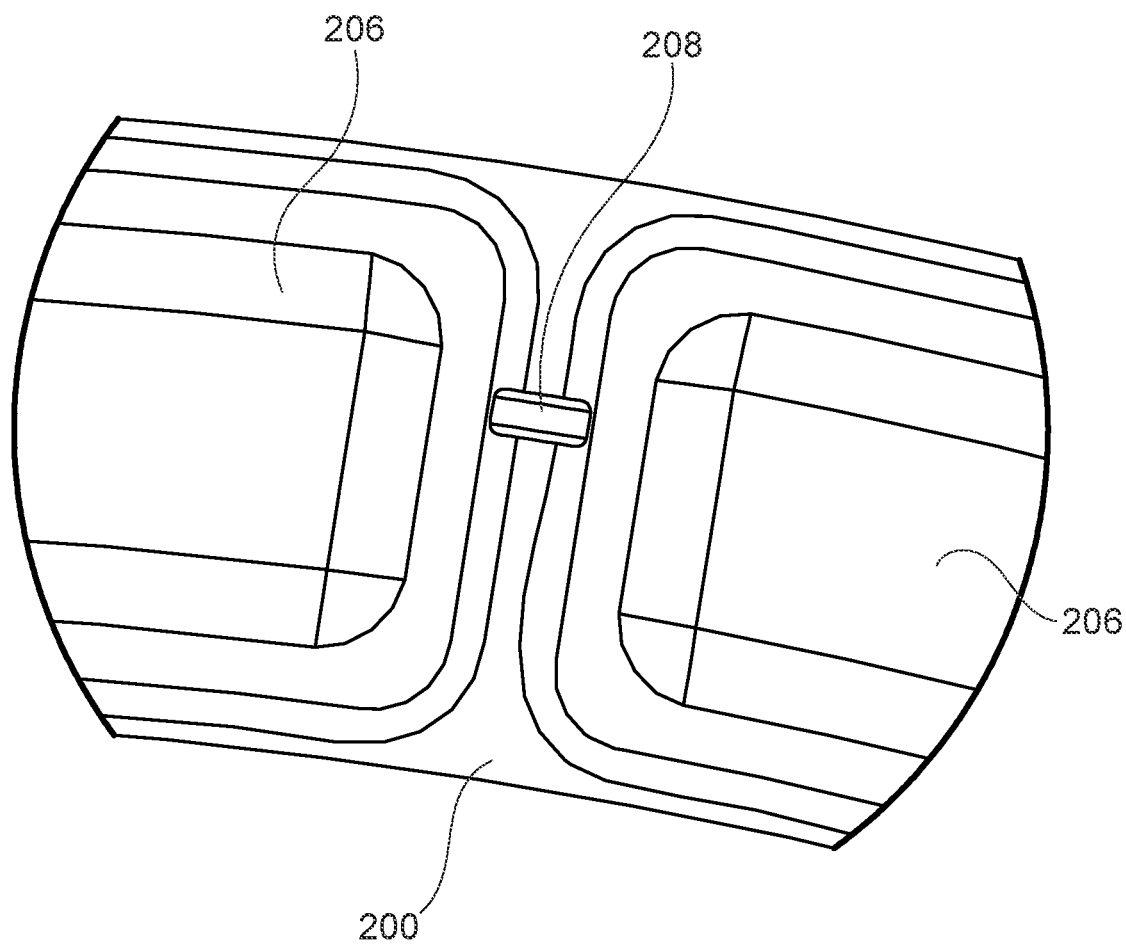
FIG. 30 is a close-up view of the structure indicated by circle 30 in FIG. 29.
Figure 31:
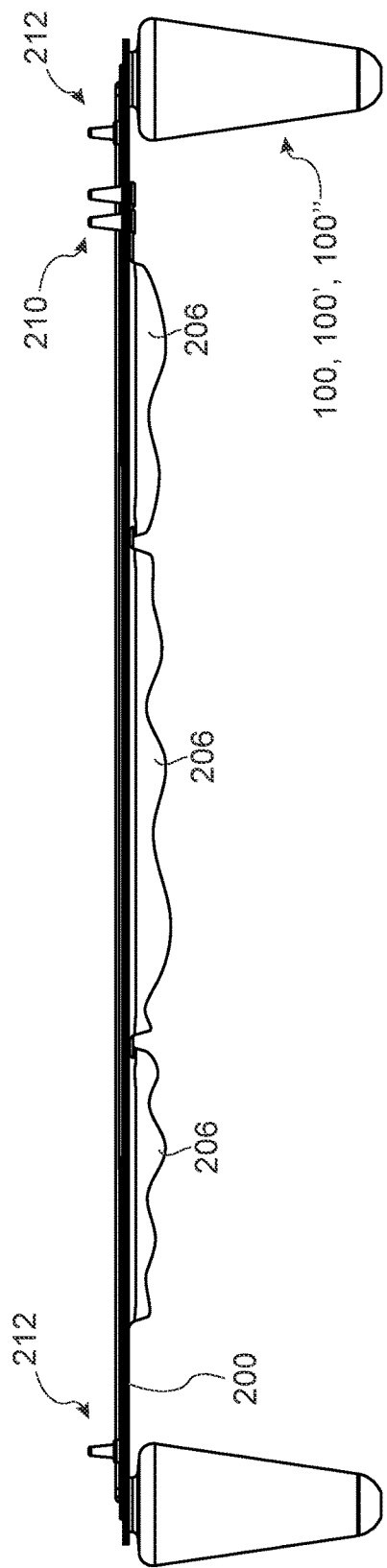
FIG. 31 is a top view of the assembly in FIG. 27, in a deflated configuration.
Figure 32:
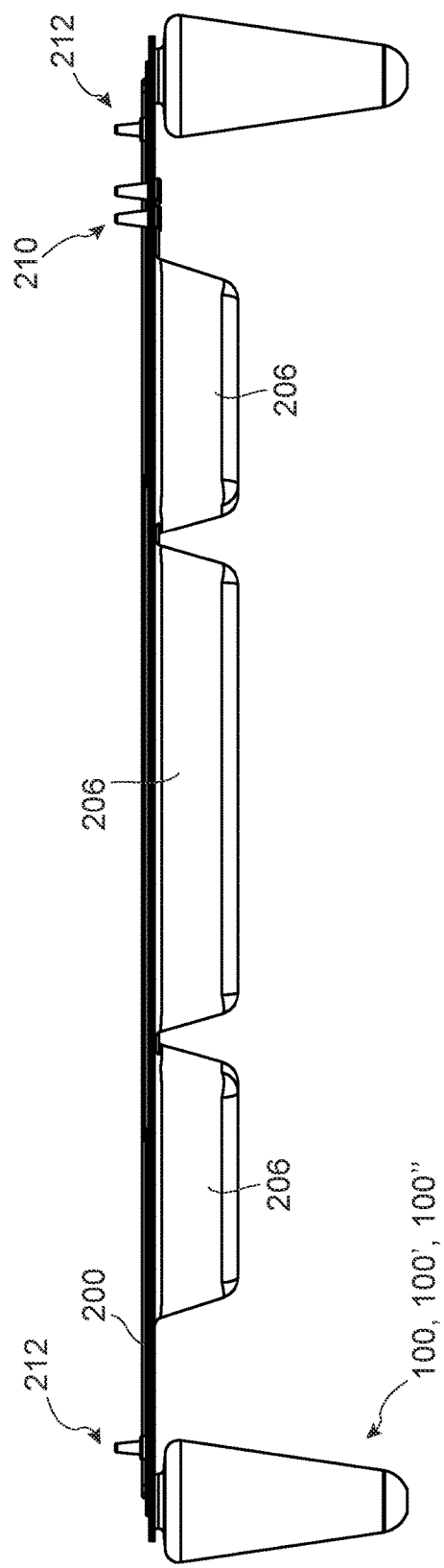
FIG. 32 is a top view of the assembly in FIG. 27, in an inflated configuration.
Figure 33:
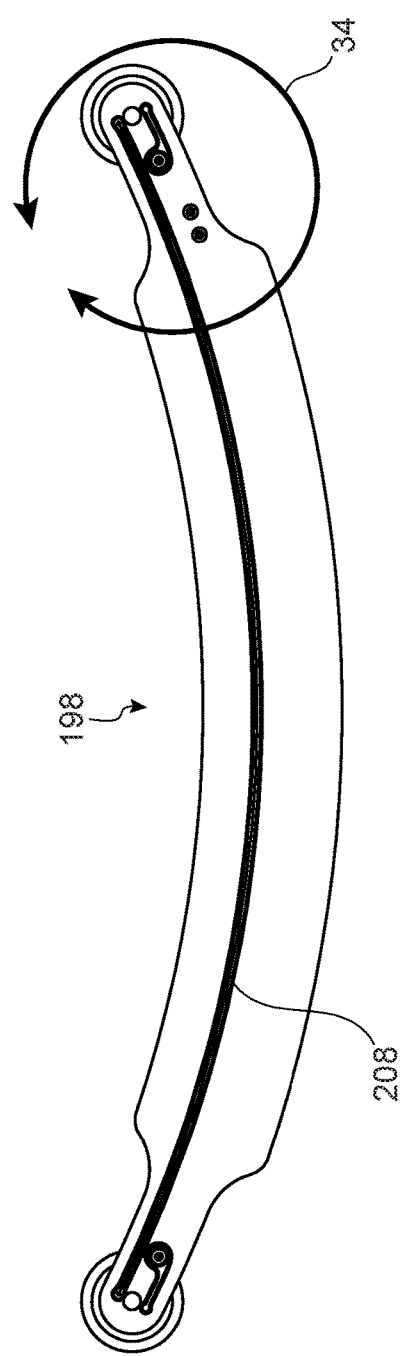
FIG. 33 is a rear view of the assembly in FIG. 27.
Figure 34:
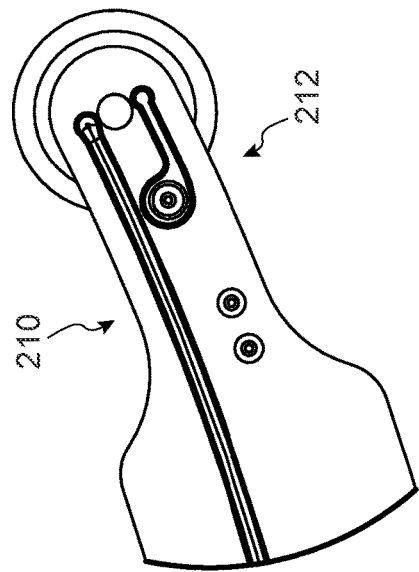
FIG. 34 is a close-up view of the structure indicated by circle 34 in FIG. 33.
Figure 35:
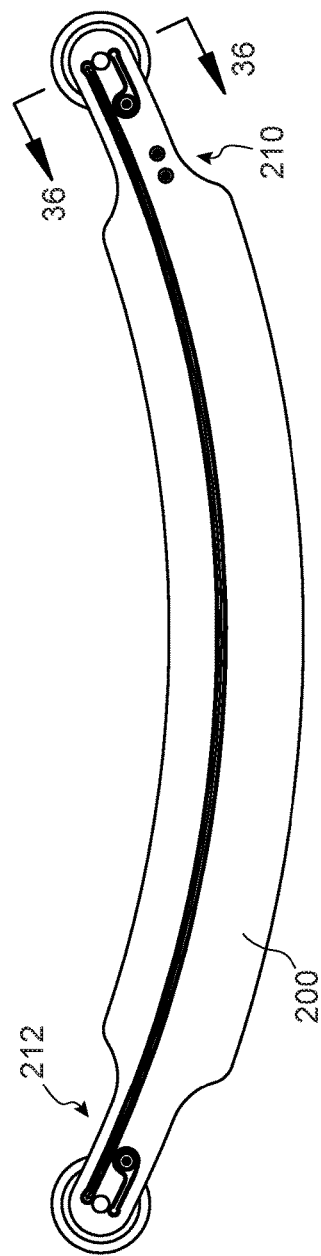
FIG. 35 is a rear view of the assembly in FIG. 27.
Figure 36:
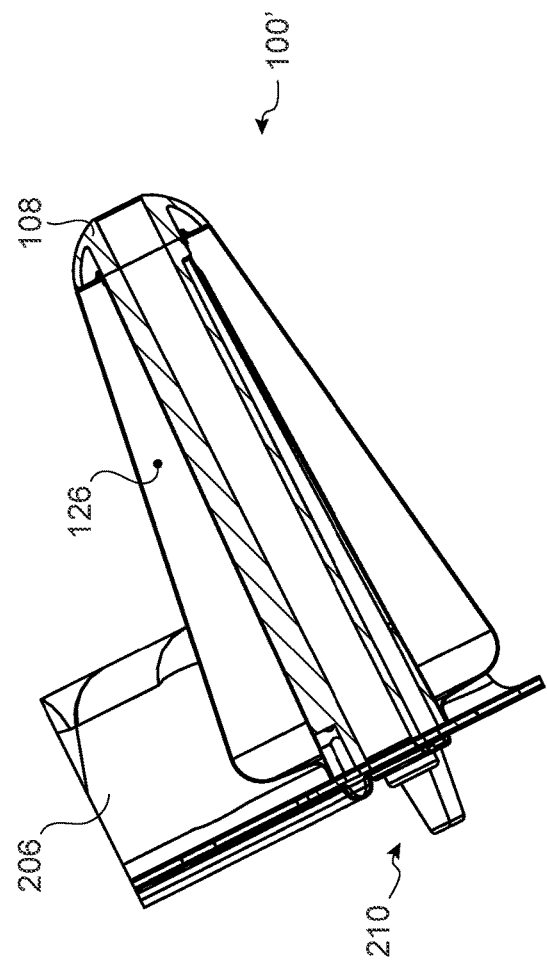
FIG. 36 is the cross-section view indicated at section 36-36 in FIG. 35, and looking in the direction of the arrows.

With particular reference to FIG. 23, working fluid 128 may be introduced to port 122 and guided along fluid conduit 184 to enter cavity 126 through an entrance/exit orifice 186 in balloon 160 (e.g., FIG. 21) near the distal end of the inserted part. Working fluid 128 then flows proximally through cavity 126 and is collected through balloon exit/entrance 188 for conveyance through conduit 190, and finally exits the heat exchanger through port 124. As illustrated in FIGS. 24 and 26, the double-walled balloon 160 is affixed to the core 140 in a fluid-tight connection at orifices 186 and 188. The illustrated arrangement operates to promote flow of the working fluid 128 in a length axis 112 direction such that working fluid 128 flows through the heat transfer area predominately from the distal end toward the proximal end of the heat transfer area, or from the proximal end 118 toward the distal end of the inserted portion 104.

It is within contemplation to provide alternative conduit path(s) for working fluid (which do not rely upon a balloon wall as a portion of conduit construction). For example, conduit 184 may be configured as being inherently closed along an extended path to an orifice at a distal end of the insertable part 104. The double-walled balloon 160 can then be replaced by a single-wall balloon to form cavity 126. The proximal end of the alternative balloon may be affixed to the core, an internal or external flange of the proximal end cap 116 to define a boundary perimeter for cavity 126. The material of construction for a balloon 160 may be opaque, translucent, or transparent. For cases where the balloon is translucent or transparent, it is contemplated that it is possible to view the structures of the ear optically thru the balloon, and/or other elements of a heat exchanger.

The direction of flow for working fluid 128 in the alternative described arrangement remains aligned with a length axis 112 through the heat transfer area. That is because least one fluid-directing conduit element (e.g., 184) associated with at least one of the input port and the output port is arranged to promote flow of the working fluid in a length axis direction such that working fluid flows through the heat transfer area predominately from the proximal end toward the distal end of the inserted portion, or, from the distal end toward the proximal end of the heat transfer area.

It is within contemplation that a temperature monitoring transducer 190 (e.g., FIG. 23) is operably disposed in-circuit with a heat exchanger 100, 100', 100", etc. to infer temperature of a portion of an ear canal. The temperature monitor 190 may be disposed inside the heat exchanger, carried by the heat exchanger, or in-line with any of the plumbing conduits that carry working fluid 128. Further, a pressure sensor 192 is desirably associated with a heat exchanger 100" to ensure proper filling and safe operating pressure. For additional safety, the heat exchanger may include design elements to control depth of device insertion into the ear canal, and to prevent expansion of the balloon 160 into the ear drum.

With reference to FIGS. 27-39, one or more heat exchangers (e.g., 100, 100', 100") may be arranged in an assembly, generally 198, including an elongate support band 200. Assembly 198 generally facilitates holding the heat exchanger(s) in an installed registration with respect to one or more ear canals. A currently preferred support band 200 is deformable to provide an arcuate shape in which to receive a human head to dispose a first heat exchanger in installed registration in one ear canal and a second heat exchanger in installed registration in the other ear canal. Support band 200 may be biased by a resilient and elastic element toward a desired assembled arcuate position.

Illustrated band 200 includes a heat exchanger, such as 100, 100', or 100", at a first end, generally 202, and a second heat exchanger at a second end, generally 204, of the band 200. One or more bladders 206 may be carried at an intermediate portion of band 200. When a bladder 206 is present, on or more coupling port, generally 210, is typically included to provide desired inflation of a bladder 206.

Band 200 may be constructed to include a multi-layer flexible polymer laminate, which can be embodied by stacked layers of membrane-like film. Layers of e.g., die- or laser-cut film, can be welded, bonded, or otherwise joined to form a substrate to hold heat exchangers (typically, one/ear). Heat exchangers may be separated by a band 200 that may include one or more fluid pathways 208 between each heat exchanger. The band 200 may also incorporate extra fluid bladders 206, or regional compartments that can be either hydraulically, or pneumatically inflated (independent from the heat exchangers) as a method to adjust the bulk fit of the entire assembly 198 to provide comfort or some other desired mechanical stability for the device as it is installed on the human head.

When present, welded/joined pathways within the laminate layers can allow the device 198 to be configured such that each heat exchanger can be fluidically independent (e.g., hydraulically in parallel) or connected in hydraulic series. Some layers of the laminate may be thermally insulating, others may be thermally conductive. It is also contemplated that embodiments may incorporate yet additional fluid bladders that could be inflated either hydraulically or pneumatically to establish insulated regions of an assembly 198 over/through which the working fluid circulating path may pass.

Figure 37:
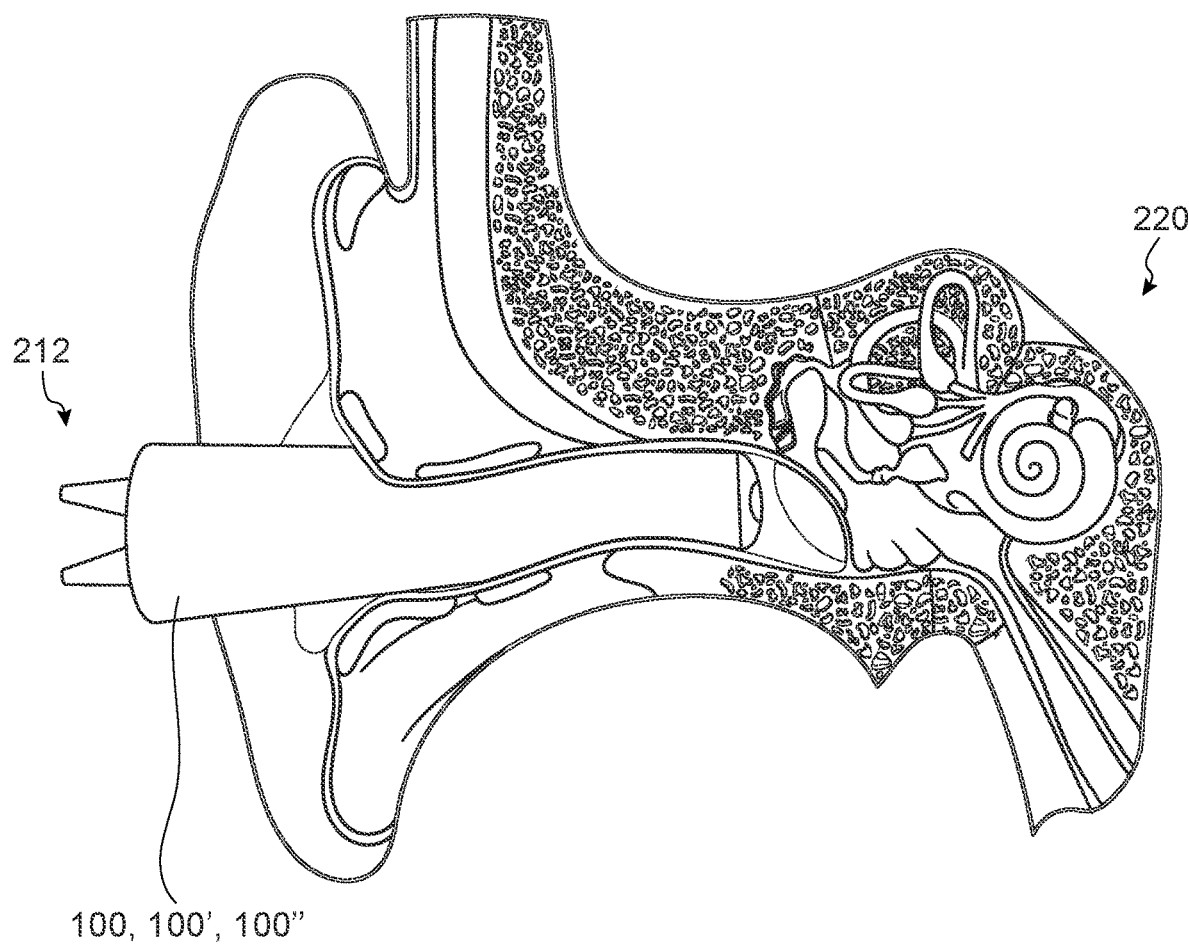
FIG. 37 is a cross-section view of a portion of a human skull with an installed heat exchanger in the ear canal.

FIG. 37 illustrates a cross-section through a portion of a human skull and ear, with an installed heat exchanger according to certain principles of the instant invention. Proximity of the installed heat exchanger to the cochlea, generally indicated at 220, is clearly illustrated. Because the distal end of an inserted part is closest to the cochlea 220, circulation of working fluid is desirably encouraged at, or near to, the distal end. Also illustrated is a degree of conformability expected by certain embodiments to present a heat transfer surface in contacting conformance to the nonlinear shape of an ear canal.

Figure 38:
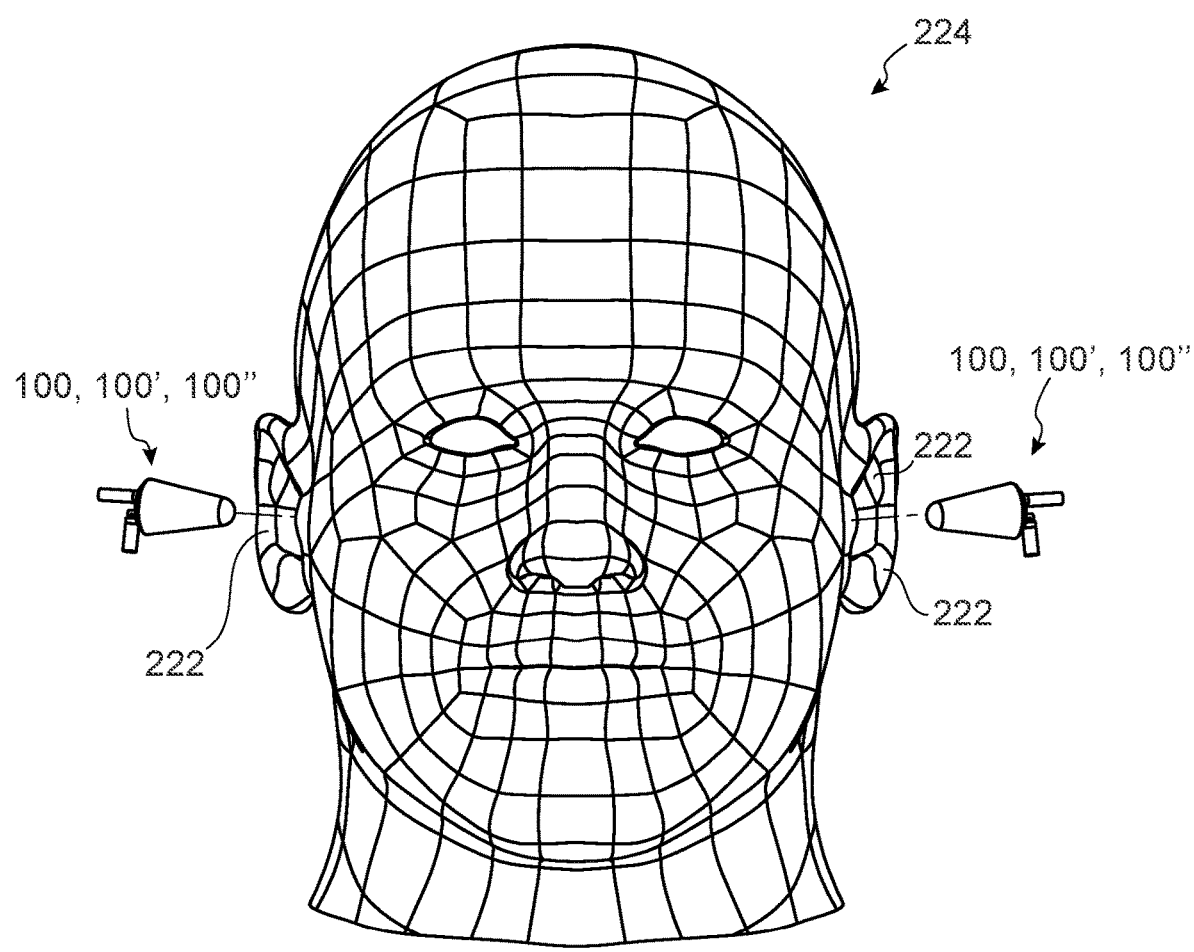
FIG. 38 is a front view in elevation of a human head and heat exchangers.
Figure 39:
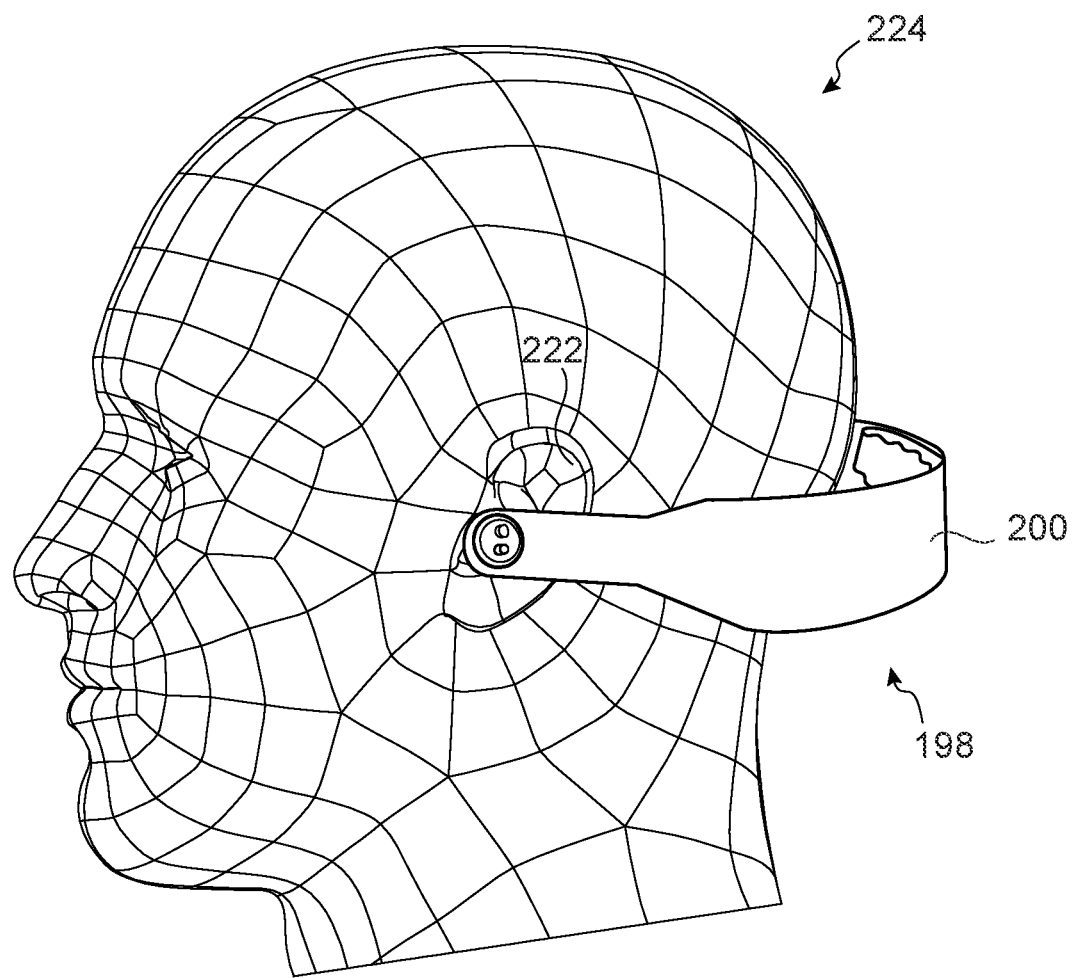
FIG. 39 is a side view in elevation of a human head and an installed heat exchanger that is carried by a band element.
Figure 40:
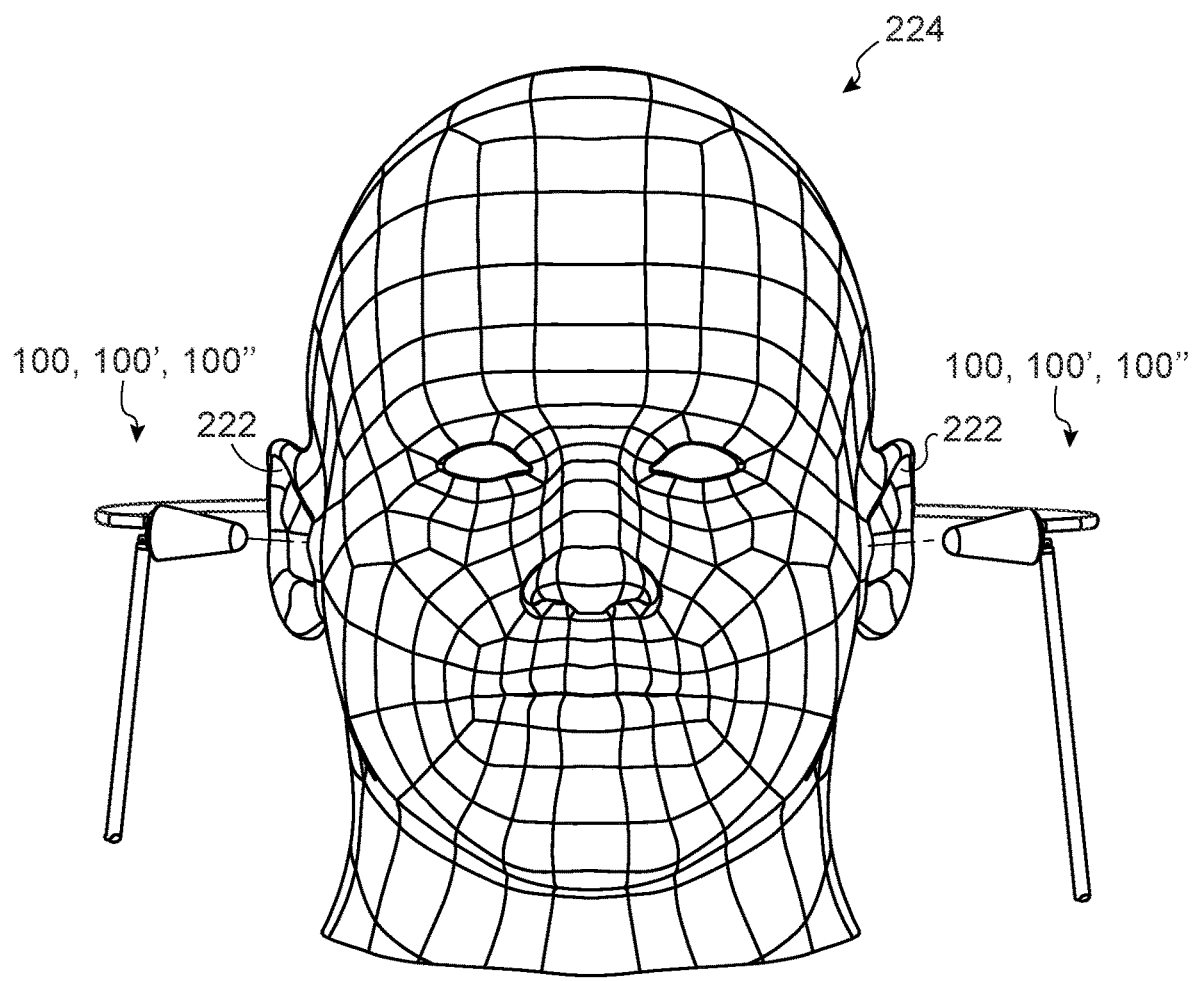
FIG. 40 is a front view in elevation of a human head and heat exchangers.
Figure 41:
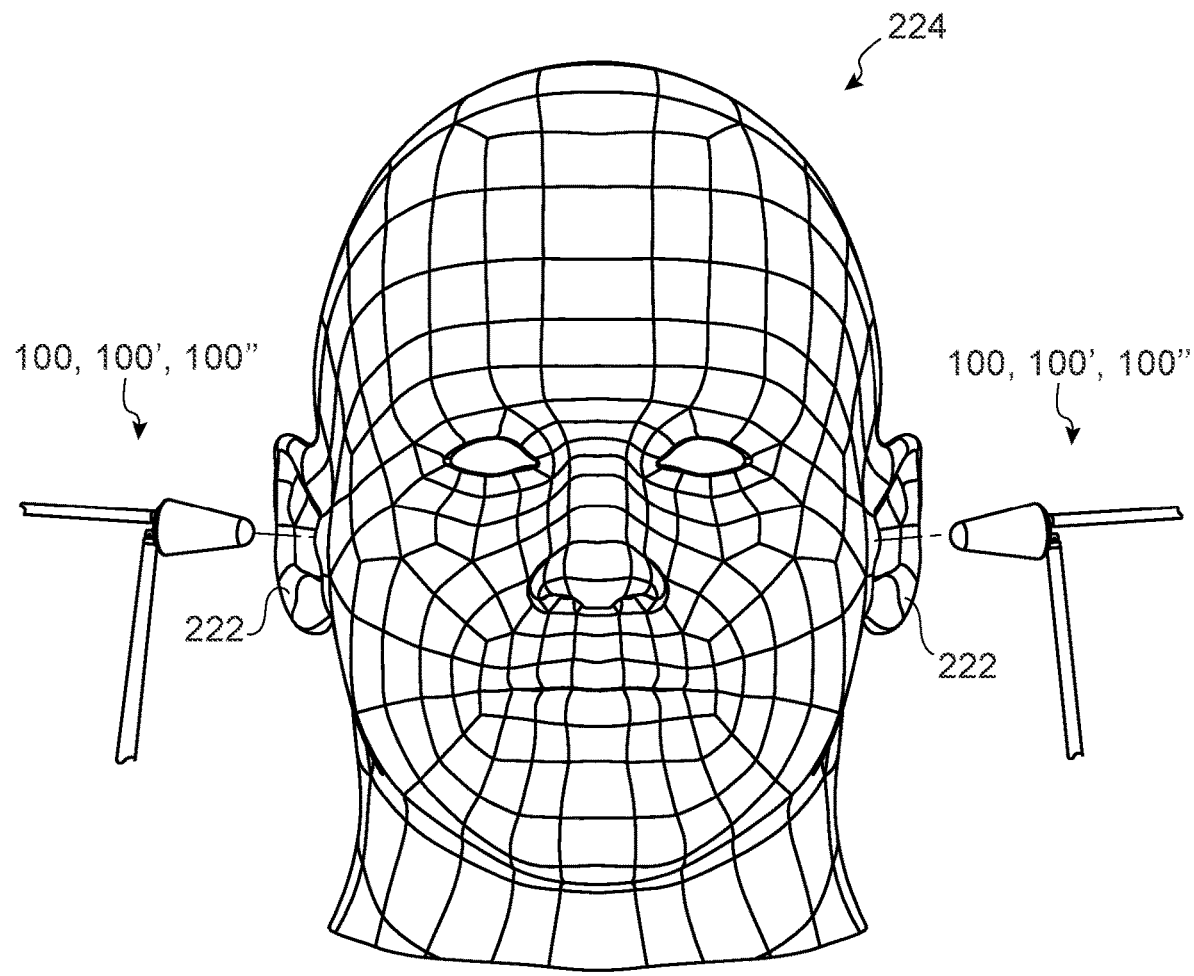
FIG. 41 is a front view in elevation of a human head and heat exchangers.

With reference to FIG. 38, one or more embodiment of a heat exchanger (e.g., 100, 100', 100"), may be inserted into one or more ear 222 of a human head, generally 224 to apply hypothermal therapy to internal ear structure. As illustrated in FIG. 39, sometimes a band 200 may be employed to facilitate holding the heat exchange(s) in an installed position. FIG. 40 illustrates a plumbing arrangement to place a pair of heat exchangers in fluidic series. FIG. 41 illustrates the case where the heat exchangers are in separate fluid circuits, and may be in parallel.

While aspects of the invention have been described in particular with reference to certain illustrated embodiments, such is not intended to limit the scope of the invention. The invention for which a monopoly position is currently desired is indicated by the appended claims rather than by the foregoing description. All changes which come within the meaning and range of equivalency of the claims are to be embraced within their scope.

The present invention may be embodied in other specific forms without departing from its spirit or essential characteristics. For one example, one or more element may be extracted from one described or illustrated embodiment and used separately or in combination with one or more element extracted from one or more other described or illustrated embodiment(s), or in combination with other known structure. The described embodiments are to be considered as illustrative and not restrictive. Obvious changes within the capability of one of ordinary skill are encompassed within the present invention.

What is claimed is:

1. An apparatus, comprising:
a first heat exchanger with an insertable part configured and arranged to fit into an ear canal of a human for disposition exterior to the ear drum associated with that ear canal, the first heat exchanger comprising:
a heat transfer surface disposed radially with respect to a length axis of the first heat exchanger, the heat transfer surface having transverse flexibility to deflect and conform for contact to a generally cylindrical heat transfer area of the inner surface of the ear canal in proximity to the ear drum;
a cavity disposed radially exterior to a hollow core and extending proximally from an anchor, the anchor being between the core and a wall associated with the heat transfer surface, the anchor being associated with a distal end of the insertable part to facilitate operation of the apparatus, along a portion of the length axis, the cavity being configured and arranged to receive a working fluid for disposition of the fluid in operable proximity to the heat transfer surface;
a fluid input port in fluid communication with the cavity to introduce the working fluid into the cavity, a proximal portion of the input port being configured to couple with a first end of a fluid-transporting conduit; and
a fluid output port in fluid communication with the cavity to exhaust the working fluid, a proximal portion of the output port being configured to couple with a second end of a fluid-transporting conduit.

2. The apparatus according to claim 1, wherein:
the first heat exchanger further comprises a non-traumatic tip disposed at a distal inserted end.

3. The apparatus according to claim 2, wherein:
the non-traumatic tip is configured to provide a proximal rim disposed radially spaced-apart from a distal anchor of the heat transfer surface.

4. The apparatus according to claim 1, wherein:
the first heat exchanger further comprises a sonic conduit extending through the hollow core to an opening associated with the distal end of the inserted portion, the sonic conduit being configured and arranged to provide an unobstructed air path from exterior the ear and exiting in an axial direction toward the ear drum.

5. The apparatus according to claim 1, wherein:
the first heat exchanger further comprises a proximal end cap associated with a proximal end of the core, the proximal end cap to provide grippable structure to facilitate tool-free removal of the inserted portion from an ear canal.

6. The apparatus according to claim 1, wherein:
at least one fluid-directing conduit element associated with one of the input port and the output port is arranged to promote flow of the working fluid in a length axis direction such that working fluid flows through the heat transfer area predominately from the proximal end toward the distal end of the inserted portion, or, from the distal end toward the proximal end of the heat transfer area.

7. The apparatus according to claim 6, wherein:
the heat transfer surface comprises a portion of a balloon, a proximal balloon end being affixed either to the proximal end of the core or to structure associated with a proximal end cap.

8. The apparatus according to claim 7, wherein:
the core is generally annular and elongate with an exterior surface disposed spaced apart as a radial function from the length axis, an inner surface being spaced apart from the length axis to provide a sonic conduit configured and arranged to provide an unobstructed air path from exterior the ear toward the ear drum.

9. The apparatus according to claim 8, wherein:
the balloon is a generally annular balloon; and
an inner wall of the balloon comprises an input port opening and an output port opening, the input port opening being arranged for fluid-tight communication with the input port, the output port opening being arranged for fluid-tight communication with the output port.

10. The apparatus according to claim 1, wherein:
the fluid input port and the fluid output port are disposed on opposite sides of the core, the core comprising a portion extending from the proximal end of the insertable part toward the distal end of the insertable part, the core to promote fluid travel through the cavity in a length direction of the inserted portion.

11. The apparatus according to claim 1, further comprising:
a second heat exchanger with an insertable portion configured and arranged for installation in the other ear canal of the human; and
a temperature monitoring transducer associated with at least one of the first heat exchanger and the second heat exchanger to infer temperature of a portion of an ear canal.

12. The apparatus according to claim 11, further comprising:
an elongate support band extending between a first end and a second end, the first heat exchanger being held in association with the first end, the second heat exchanger being held in association with the second end, the support band being deformable to provide an arcuate shape in which to receive a human head to dispose the first heat exchanger in installed registration in one ear canal and the second heat exchanger in installed registration in the other ear canal; and
plumbing conduits in circuit to convey working fluid from a remote temperature controller toward and away from each heat exchanger.

13. The apparatus according to claim 11, further comprising:
a pneumatic bladder carried at an intermediate position by the support band, the bladder being inflatable to provide a variable-size filler between a portion of the support band and a human head received in the arcuate shape.

14. An apparatus, comprising:
a first heat exchanger with an insertable part configured and arranged to fit into an ear canal of a human for disposition exterior to the ear drum associated with that ear canal, the first heat exchanger comprising:
a heat transfer surface disposed radially with respect to a length axis of the first heat exchanger, the heat transfer surface having transverse flexibility to deflect and conform for contact to a generally cylindrical heat transfer area of the inner surface of the ear canal;
a cavity extending along a portion of the length axis, the cavity being configured and arranged to receive a working fluid for disposition of the fluid in operable proximity to the heat transfer surface;
a fluid input port in fluid communication with the cavity to introduce the working fluid, a proximal portion of the input port being configured to couple with a first end of a fluid-transporting conduit; and a fluid output port in fluid communication with the cavity to exhaust the working fluid, a proximal portion of the output port being configured to couple with a second end of a fluid-transporting conduit, wherein:

the first heat exchanger further comprises a generally annular and elongate core disposed spaced apart as a radial function from the length axis; and the first heat exchanger further comprises a proximal end cap associated with a proximal end of the core, the proximal end cap to provide grippable structure to facilitate tool-free removal of the inserted portion from an ear canal, wherein:

the proximal end cap provides a cantilever base from which the core extends, an opening at the proximal end of the proximal end cap to provide fluid communication to a sonic conduit through the core and extending to an opening associated with the distal end of the inserted portion, the sonic conduit being configured and arranged to provide an unobstructed air path from exterior the ear toward the ear drum.

15. The apparatus according to claim 14, further comprising:

a first fluid path to provide fluid communication with one of the input fluid port and the output port, a portion of the first fluid path defined by, and extending through, a portion of the core; and a second fluid path to provide fluid communication with the other one of the input fluid port and the output port.

16. The apparatus according to claim 15, wherein:

the first fluid path extends to an opening associated with a distal portion of the core.

17. The apparatus according to claim 15, wherein:

the first fluid path extends to an opening associated with a proximal portion of the core.

18. An apparatus, comprising:

a first heat exchanger with an insertable part configured and arranged to fit into an ear canal of a human for disposition exterior to the ear drum associated with that ear canal, the first heat exchanger comprising:

a heat transfer surface disposed radially with respect to a length axis of the first heat exchanger, the heat transfer surface having transverse flexibility to deflect and conform for contact to a generally cylindrical heat transfer area of the inner surface of the ear canal;

a cavity extending along a portion of the length axis, the cavity being configured and arranged to receive a working fluid for disposition of the fluid in operable proximity to the heat transfer surface;

a fluid input port in fluid communication with the cavity to introduce the working fluid, a proximal portion of the input port being configured to couple with a first end of a fluid-transporting conduit; and a fluid output port in fluid communication with the cavity to exhaust the working fluid, a proximal portion of the output port being configured to couple with a second end of a fluid-transporting conduit, wherein:

the first heat exchanger further comprises a generally annular and elongate core disposed spaced apart as a radial function from the length axis and, wherein:

the heat transfer surface comprises a portion of a generally annular balloon affixed at a proximal balloon end to the proximal end of the core, the exterior annular wall being transversely flexible to accommodate to a variable wall conformation of the ear canal, a portion of the inner annular wall being affixed to the core.

* * * * *